United States Patent [19]

Saaski et al.

[11] Patent Number: 4,778,987

[45] Date of Patent: Oct. 18, 1988

[54] OPTICAL MEASURING DEVICE USING A SPECTRAL MODULATION SENSOR HAVING AN OPTICALLY RESONANT STRUCTURE

[76] Inventors: Elric W. Saaski, 13338 NE. 138th Pl., Kirkland, Wash. 98034; James C. Hartl, P.O. Box 918, Snohomish, Wash. 98290

[21] Appl. No.: 914,882

[22] Filed: Oct. 3, 1986

Related U.S. Application Data

[63] Continuation-in-part of Ser. No. 628,813, Jul. 6, 1984, Pat. No. 4,678,904.

[51] Int. Cl.⁴ .............................................. G01J 3/50
[52] U.S. Cl. .................................... 250/226; 250/227; 250/231 P; 356/352
[58] Field of Search ............... 250/226, 227, 231 R, 250/231 D; 73/705, 717, 722; 356/352; 374/161, 162

[56] References Cited

U.S. PATENT DOCUMENTS

| | | | |
|---|---|---|---|
| 3,267,932 | 8/1966 | Valliere | 128/2.05 |
| 3,580,082 | 5/1971 | Strack | 73/406 |
| 4,158,310 | 6/1979 | Ho | 73/705 |
| 4,160,600 | 7/1979 | Luke | 356/352 |
| 4,163,382 | 8/1979 | Amer | 250/351 |
| 4,194,877 | 3/1980 | Peterson | 8/4 |
| 4,200,110 | 4/1980 | Peterson et al. | 128/634 |
| 4,201,222 | 5/1980 | Haase | 128/634 |
| 4,210,029 | 7/1980 | Porter | 73/705 |
| 4,249,076 | 2/1981 | Bergstrom et al. | 250/227 |
| 4,270,050 | 6/1981 | Brogardh | 250/231 R |
| 4,275,296 | 6/1981 | Adolfsson | 250/227 |
| 4,278,349 | 7/1981 | Sander | 356/44 |
| 4,281,245 | 7/1981 | Brogardh | 250/227 |
| 4,307,607 | 12/1981 | Saaski et al. | 73/366 |
| 4,321,831 | 3/1982 | Tomlinson et al. | 73/705 |
| 4,329,058 | 5/1982 | James et al. | 356/352 |
| 4,356,396 | 10/1982 | Ruell et al. | 250/227 |
| 4,368,645 | 1/1983 | Glenn et al. | 73/705 |
| 4,428,239 | 1/1984 | Johnston | 73/705 |
| 4,430,565 | 2/1984 | Brogardh et al. | 250/227 |
| 4,437,761 | 3/1984 | Kroger et al. | 356/44 |
| 4,446,366 | 5/1984 | Brogardh et al. | 250/227 |
| 4,451,730 | 5/1984 | Brogardh et al. | 250/227 |
| 4,487,206 | 12/1984 | Aagard | 128/667 |
| 4,558,217 | 12/1985 | Alves | 250/227 |
| 4,581,530 | 4/1986 | Brogardh et al. | 250/231 R |
| 4,678,904 | 7/1987 | Saaski et al. | 250/226 |
| 4,689,483 | 8/1987 | Weinberger | 374/162 |

OTHER PUBLICATIONS

"Fiber Optic Blood Pressure Catheter with Frequency Response from D.C. Into the Audio Range", by F. J. Clark et al, *Proceedings of the National Electronics Conference*, 1965, pp. 213–216.

(List continued on next page.)

*Primary Examiner*—David C. Nelms
*Attorney, Agent, or Firm*—Gregory W. Moravan

[57] ABSTRACT

Physical changes induced in the spectral modulation sensor's optically resonant structure by the physical parameter being measured cause microshifts of its reflectivity and transmission curves, and of the selected operating segment(s) thereof being used, as a function of the physical parameter being measured. The operating segments have a maximum length and a maximum microshift of less than about one resonance cycle in length for unambiguous output from the sensor. The input measuring light wavelength(s) are selected to fall within the operating segment(s) over the range of values of interest for the physical parameter being measured. The output light from the sensor's optically resonant structure is spectrally modulated by the optically resonant structure as a function of the physical parameter being measured. The spectrally modulated output light is then converted into analog electrical measuring output signals by detection means. In one form, a single optical fiber carries both input light to and output light from the optically resonant structure. When more than one input measuring light wavelength is used, means may also be provided to divide the input light wavelengths into two portions and then take the ratio thereof. This provides several advantages simultaneously, such as enabling longer operating segments and microshifts to be used for greater sensitivity or detection range, and also eliminates certain errors caused by fluctuations in input light intensity or by changes in light intensity caused by optical fiber bending and optical fiber connectors.

30 Claims, 10 Drawing Sheets

OTHER PUBLICATIONS

"Medical Applications of Fiber Optics", by M. L. Polanyi, *Digest of the 6th International Conference on Medical Electronics and Biological Engineering*, 1965, Tokyo, pp. 598–599.

"Measurement of the Second Derivative of Left Ventricular Pressure Using a Fiber Optic Catheter", by B. Letac et al, *Proceedings of the Society of Experimental Bio-Medics*, 1968, pp. 63–66.

"A Fiberoptic Catheter for the Measurement of Intravascular Pressures and Sounds", by A. Ramirez et al, *Abstracts of the 41st Scientific Sessions*, 1968, p. VI-160.

"Direct Conversion of Sound Waves to Light Waves Using Interferometric Techniques", by L. S. Sheiner et al, *IBM Technical Disclosure Bulletin*, vol. 22, No. 1, June 1979.

"Fiber-Optic Probe for in Vivo Measurement of Oxygen Partial Pressure" by John I. Peterson et al, *Analytical Chemistry*, vol. 56, Jan. 1984, pp. 62–66.

"Fiber Optic pH Probe for Physiological Use" by John I. Peterson et al, *Analytical Chemistry*, May 1980, pp. 864–869.

"Fiber Optic Sensors for Biomedical Applications" by John I. Peterson et al, *Science*, vol. 224, No. 4645, Apr. 1984, pp. 123–12.

*Fundamanetals of Optics*, by Francis A. Jenkins, McGraw-Hill Book Co., 1976, pp. 301–308.

*Introduction to Modern Optics*, by Grant R. Fowles, Holt, Rinehart & Winston, Inc., 1975, pp. 90–97.

*Optics*, by Eugene Hecht, Addison-Wesley Publishing Company, 1979, pp. 307–311.

First International Converence on Optical Fibre Sensors, 26th–28th Apr. 1983, London, GB, pp. 122–125; E. R. Cox et al; "Fibre Optic Colour Sensors Based on Fabry-Perot Interferometry"; pp. 122, 124; FIG. 2.

First International Conference on Optical Fibre Sensors, 26th–28th, Apr. 1983, London, GB, pp. 6–9; W. H. Quick et al; "Fiber Optics Sensing Techniques"; p. 6, FIGS. 1, 2.

EP-A-O 013 974 (Rockwell Int. Corp.), pp. 3,6,7,10,13; FIGS. 3, 4 published Aug. 6, 1980.

WO-A-8 302 327 (MTA Kozponti Fizikai Dutato Intezete), pp. 5, 6, 9 published Jul. 7, 1983.

EP-A-O 058 801 (Imperial Chemical Ind.), published Sep. 1, 1982.

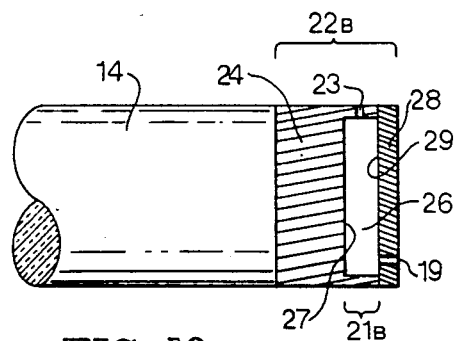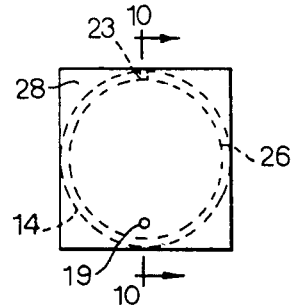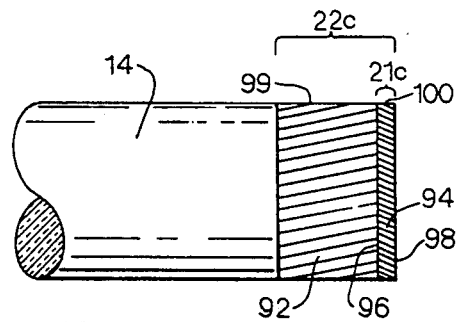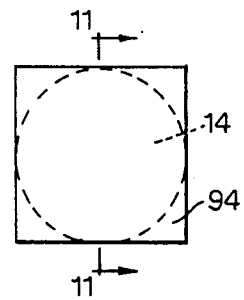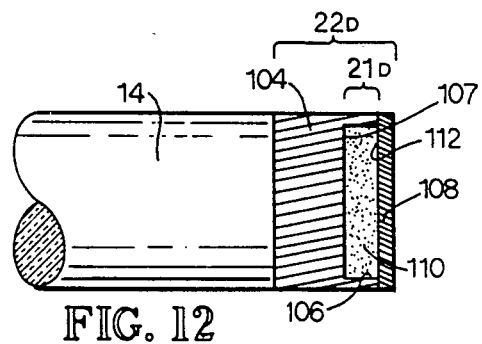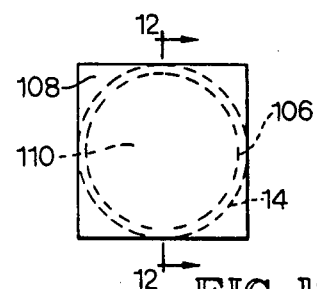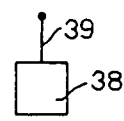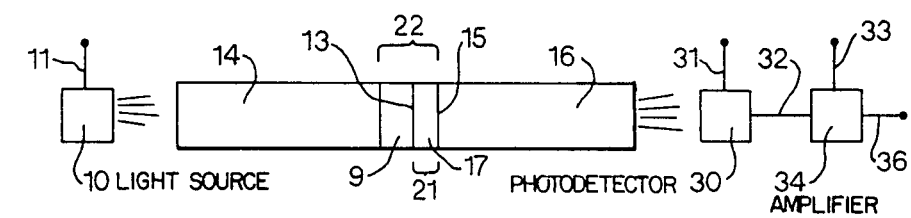

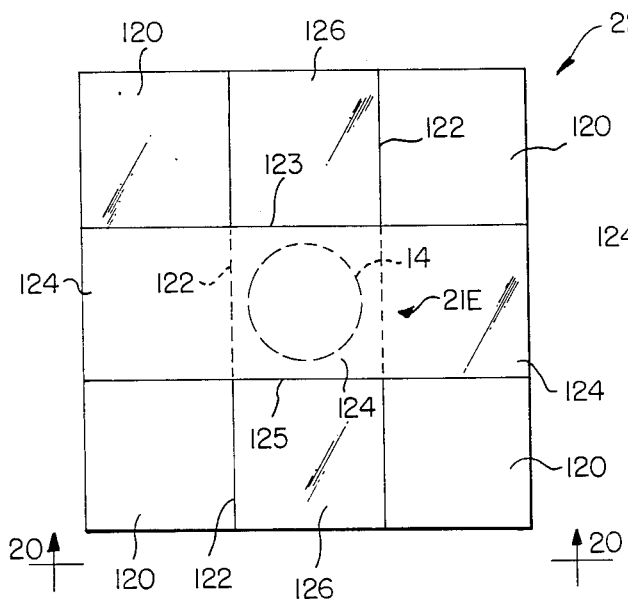
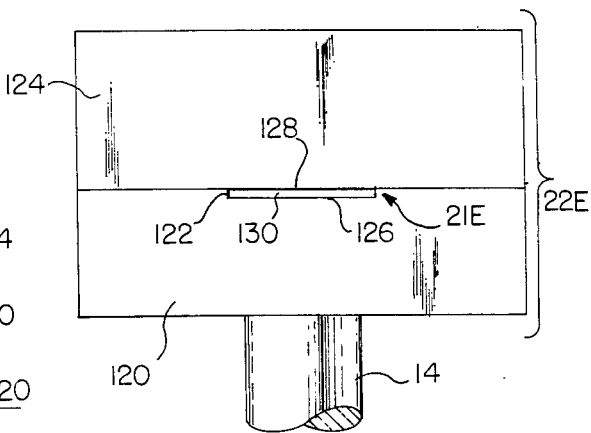
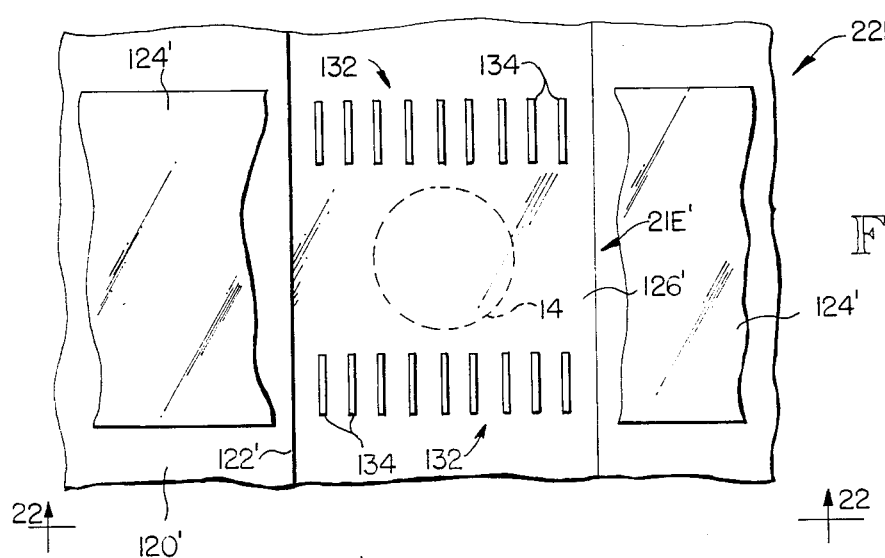
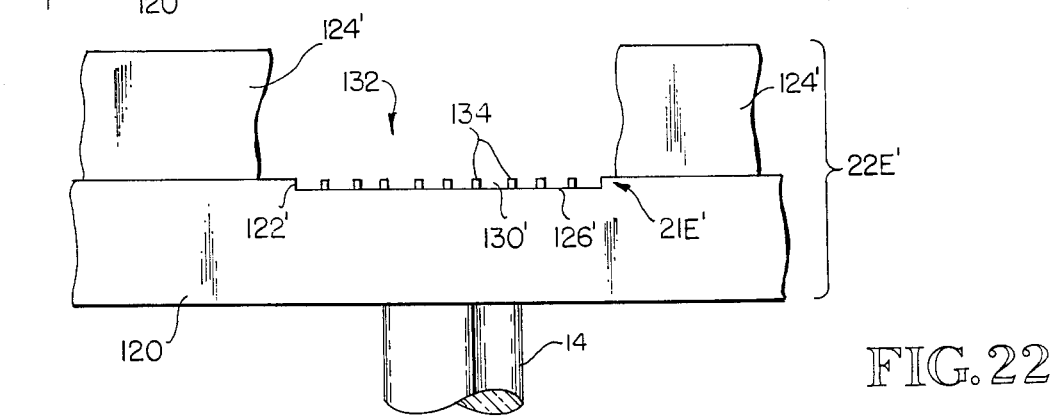

OPTICAL MEASURING DEVICE USING A SPECTRAL MODULATION SENSOR HAVING AN OPTICALLY RESONANT STRUCTURE

This is a continuation-in-part patent application of parent patent application Ser. No. 628,813, filed July 6, 1984, now U.S. Pat. No. 4,678,904.

FIELD OF INVENTION

The invention relates to optical devices for sensing and measuring various physical parameters. More particularly, this invention relates to an optical device having a spectral modulation sensor in which the physical parameter being measured causes spectral changes in the reflectivity and/or transmission of the sensor's optically resonant structure, thereby spectrally modulating the output light from the sensor as a function of the physical parameter being measured.

SUMMARY OF THE INVENTION

Some objects of the invention are to provide a low cost, stable, reliable and accurate optical measuring device for detecting and measuring various physical parameters such as, by way of non-limiting example, pressure, temperature, gas density, and various chemical species.

Further objects of the invention are to provide such a device which is immune, during use of the device, to changes in intensity of the light source and to changes in light transmission intensity due to optical fiber bending and due to optical connector light loss.

A further object of the invention is to provide such a device which provides an analog type output when measuring the physical parameter being measured, in order to provide a higher degree of resolution in measuring the physical parameter being measured as compared to a device which provides a digital type output.

Another object of the invention is to provide such a device having a spectral modulation sensor which measures the physical parameter being measured by utilizing microshifts in the operating segment(s) of the reflectivity and/or transmission curve of the sensor's optically resonant structure caused by the physical parameter being measured.

Another object of the invention is to provide such a device having a spectral modulation sensor which accurately measure the physical parameter being measured by utilizing operating segment(s) which are less than about one resonance cycle in length and which are microshifted less than about one resonance cycle; and by utilizing measuring input light wavelength(s) which fall within the operating segment(s) over substantially the range of values of interest for the physical parameter being measured.

A further object of the invention is to provide such a device whose spectral modulation sensor is small enough to be mounted directly on the end of a single optical fiber; and which thus utilizes all light emanating from that optical fiber, for greater sensitivity.

Other objects of the invention are to provide such a device having a spectral modulation sensor which is small enough to be inserted readily into selected blood vessels of the human body, and which is non-toxic to the human body.

Another object of the invention is to provide such a device in which, by suitable design of the optically resonant structure in the device's spectral modulation sensor, the output measuring signal will either vary either directly or inversely with changes in value of the sensed physical parameter.

In basic form, the invention comprises a light source, a light transmission means, a spectral modulation sensor having an optically resonant structure, and detection means for converting the output light from the spectral modulation sensor into electrical signals.

The light transmission means comprises an input optical fiber, an optical beam splitter, an optical fiber connector, a sensor optical fiber, and an output optical fiber. The optical beam splitter and optical fiber connector optically connect the sensor optical fiber with the input and output optical fibers.

Input light from the light source travels sequentially through the input optical fiber, optical fiber beam splitter, optical fiber connector and sensor optical fiber into the spectral modulation sensor. Output light from the spectral modulation sensor travels sequentially through the sensor optical fiber, optical fiber connector, optical fiber beam splitter and output optical fiber to the detection means.

Thus, a single optical fiber, namely the sensor optical fiber, acts to both convey input light to the spectral modulation sensor and to convey output light from the spectral modulation sensor. This simplifies the optical measuring device, reduces its size and cost, and increases its reliability as compared to a system employing two optical fibers, each separately connected to the spectral modulation sensor, to input light to the spectral modulation sensor and output light from the spectral modulation sensor, respectively.

As has been mentioned, the spectral modulation sensor has, as its active element, an optically resonant structure. The present invention contemplates several different forms of the spectral modulation sensor which are capable of detecting different physical parameters depending on the particular nature of their optically resonant structures.

In general, an optically resonant structure comprises a pair of separated reflective surface, with the reflectivity and transmission of the optically resonant structure being functions of its optically sensitive physical characteristics, such as the distance between its reflective surfaces, the optical characteristics of its reflecting surfaces, and the index of refraction of whatever is between its reflective surfaces.

Thus, if at least one of the optically sensitive physical characteristics of a particular spectral modulation sensor's optically resonant structure are altered by the physical parameter being measured, then the light reflected and/or transmitted by the spectral modulation sensor will change as a function of the physical parameter being measured. Accordingly, the output light from the spectral modulation sensor will be spectrally modulated by its optically resonant structure as a function of the physical parameter being measured and carries information regarding the physical parameter being measured.

The spectrally modulated output light from the spectral modulation sensor is converted into an output electrical signal by the detection means which comprise photodetector and amplifier means. The output electrical signal provides an accurate determination of the physical parameter being measured, within a certain range of values for the physical parameter being measured, once the optical measuring device has been calibrated.

However, the basic form of the invention just described may be susceptable to measurement inaccuracies due to changes in the light source intensity and to changes in light transmission intensity due to bending of the optical fibers or due to optical connector light loss.

In a second embodiment of the invention, the above potential measurement inaccuracies are eliminated. The second embodiment is similar to the first embodiment described above, with the following changes. First, the light source is selected to emit light over at least two wavelengths, or over a band of wavelengths, and may be a light emitting diode (LED), for example. The spectral modulation sensor operates as before, with the spectral reflectivity and/or transmission of its optically resonant structure being a function of the physical parameter being measured. As before, the output light from the spectral modulation sensor is spectrally modulated by the sensor's optically resonant structure as a function of the physical parameter being measured, and carries information regarding the physical parameter being measured.

However, in the detection means the spectrally modulated output light wavelengths from the spectral modulation sensor are separated into two spectral components, each of which is separately converted into an electrical signal by photodetector means and then amplified. Finally, a divider circuit takes the ratio of these two electrical signals to provide an output signal. The output signal from the divider circuit provides an accurate determination of the physical parameter being measured, within a certain range of values for the physical parameter being measured, once the optical measuring device has been calibrated.

Importantly, the second embodiment of the invention described above is not susceptable to measurement inaccuracies due to changes in the light source intensity and to changes in light transmission intensity due to bending of the optical fibers and due to optical connector light loss. This is because such changes normally affect the two spectral components of the spectral modulation sensor's output equally. Thus, when the two electrical signals corresponding to the two spectral components of the spectral modulation sensor's output are divided in the divider circuit, such changes cancel each other out and have no effect on the output signal from the divider circuit.

The foregoing is intended to be but a brief summary of some of the objects, features, advantages and characteristics of the invention, and is not intended to be a detailed catalog thereof since these and further objects, features, advantages and characteristics will be expressly or inherently disclosed to those skilled in the art to which the invention pertains in view of all of the disclosures herein.

BRIEF DESCRIPTION OF THE FIGURES

FIG. 8 is a schematic side elevation view showing the first embodiment 22A of the spectral modulation sensor, in a partial longitudinal cross section taken along line 8—8 of FIG. 8a;

FIGS. 10, 11, and 12 are schematic side elevation views showing the second, third and fourth embodiments 22B, 22C and 22D of the spectral modulation sensor in partial longitudinal cross sections, taken along lines 10—10, 11—11 and 12—12 of FIGS. 10a—12a, respectively;

FIGS. 10a, 11a, and 12a are elevation views of the right sides of FIGS. 10, 11, and 12, respectively;

FIG. 13 is a schematic illustration of the third embodiment of the optical measuring device;

FIG. 19 is a top plan view of a fifth embodiment 22E of the spectral modulation sensor;

FIG. 20 is a side elevation view taken along line 20—20 of FIG. 19;

FIG. 21 is a partial top plan view of a modified embodiment 22E' of spectral modulation sensor 22E, with parts of cover 124' broken away to reveal filter comb structures 132;

FIG. 22 is a side elevation view taken along line 22—22 of FIG. 21;

DESCRIPTION OF THE PREFERRED EMBODIMENTS

First Embodiment of the Optical Measuring Device

Figure 1:
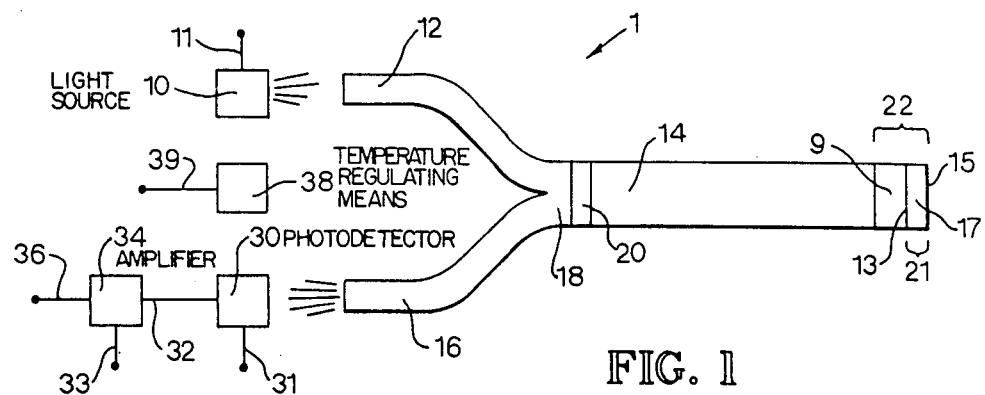
FIG. 1 is a schematic illustration of the first embodiment 1 of the optical measuring device.

The first embodiment 1 of the optical measuring device of the invention is schematically illustrated in FIG. 1. Light source 10 is for providing suitable measuring input light which may be monochromatic or which may be dispersed over two or more adjacent or non-adjacent wavelengths. Light source 10 can comprise at least one source of monochromatic light, such as a laser or a lasing diode, at least one source of two or more wavelengths, such as a light emitting diode (LED), and/or suitable optical filgers to provide the desired input light. Suitable power for light source 10 is provided by any suitable source of electrical power through conventional electrical connection means 11.

For simplicity, by way of non-limiting example, a single monochromatic light source 10, such as a lasing diode which emits light with a wavelength of 810 nm will be discussed below.

Input light from light source 10 is coupled into sensor optical fiber 14 via input optical fiber 12, optical beam splitter 18 and optical fiber connector 20.

Optically connected to the end of sensor optical fiber 14, and receiving input light therefrom, is a spectral modulation sensor 22 having an optional substrate 9 supporting an optically resonant structure 21. Substrate 9 has two purposes. First, it improves the sensitivity of optically resonant structure 21 by acting as a spacer between the end of sensor optical fiber 14 and optically resonant structure 21. Substrate 9 preferably has a thickness about equal to the diameter of sensor optical fiber 14. Improved sensitivity of optically resonant structure 21 results if substrate 9 is used, because light entering optically resonant structure 21 from sensor optical fiber 14 is relatively more collimated than if substrate 9 were omitted and sensor 22 were secured directly to the end of sensor optical fiber 14. If substrate 9 is omitted, optically resonant structure 21 may be secured directly to the end of sensor optical fiber 14. Secondly, substrate 9 serves as an aid in the manufacture of sensor 22 and in the assembly of optically resonant structure 21 to the end of sensor optical fiber 14, since as will become apparent subsequently, optically resonant structure 21 can be less than one micron thick. Preferably, substrate 9 does not play a part in spectrally modulating the measuring input light to optically resonant structure 21, but it could do so.

Optically resonant structure 21 comprises, in general, a pair of separated reflective surfaces 13, 15 with the reflectivity and transmission of the optically resonant structure being functions of its optically sensitive physical characteristics, such as the distance between its reflective surfaces 13, 15, the optical characteristics of its reflective surfaces 13, 15, and the index of refraction of whatever 17 is between its reflective surfaces 13, 15. The output light from sensor 22 is spectrally modulated by optically resonant structure 21 as a function of at least one of the optically sensitive physical characteristics of optically resonant structure 21.

Spectrally modulated output light from the sensor 22 travels sequentially through sensor optical fiber 14, optical fiber connector 20, optical beam splitter 18 and output optical fiber 16 where it is optically coupled to photodector 30.

The output signal from photodetector 30 is delivered via electrical connection means 32 to amplifier 34. The amplified output signal from amplifier 34 is delivered to output terminal 36, and provides a measurement of the physical parameter being measured.

Power from any suitable source of electrical power for photodetector 30 and amplifier 34 are provided through electrical connection means 31, 33, respectively. Parts 30–36 form detection means for converting output light from sensor 22 into a useful electrical output measuring signal at output terminal 36.

The light source 10 and photodetector 30 are typically housed within a suitable housing and provided with temperature regulating means 38 to maintain said components at a relatively constant temperature to enhance the stability and accuracy of the optical measuring device. Power from any suitable source of electrical power for temperature regulating means 38 is provided through electrical connection means 39. By way of non-limiting example, temperature regulating means 38 could comprise a resistance heating element controlled by a thermostat to maintain said components at a pre-selected temperature above normal room temperature, such as 100° F.

Theoretical Considerations for First Embodiment of Optical Measuring Device

Now that the general construction and operation of the first embodiment 1 of the invention has been considered, its theory of operation will be addressed.

Its theory of operation involves the cyclic optical nature of the reflectivity curves of its optically resonant structure 21 in response to input light and the physical parameter being measured, and how small shifts in these response curves, termed herein microshifts, can be used to sense and measure various physical phenomena such as pressure, temperature, gas density and chemical species.

By way of non-limiting example, for the simplest form of an optically resonant structure 21, namely a parallel plane optically resonant structure 21 which comprises a pair of separated parallel reflective surfaces 13, 15, the reflectivity R of parallel plane optically resonant structure 21 is known to be given by the equation:

$$R = 1 - s^2/((1-r)^2 + 4r \sin^2(\text{theta}))$$

where $s = (s_1 s_2)^{0.5}$ and $r = (r_1 r_2)^{0.5}$. The quantities $s_1$, $s_2$ are, respectively, the transmittances of reflective surfaces 13, 15, while $r_1$, $r_2$ are, respectively, the reflectances of reflective surfaces 13, 15 as seen from within parallel plane optically resonant structure 21.

The angle theta in the sine term in the above equation is known to be given by:

$$\text{theta} = 2(\text{pi})nt \cos(\text{phi})/\text{lambda} + e$$

where:
n = the refractive index of whatever 17 is between reflective surfaces 13, 15;
t = the distance between reflective surfaces 13, 15;
phi = the angle of light reflection between reflective surfaces 13, 15;
lambda = the wavelength of input light empinging on optically resonant structure 21; and
e = any phase shift caused by reflection from either reflective surface 13, 15.

Figure 2:
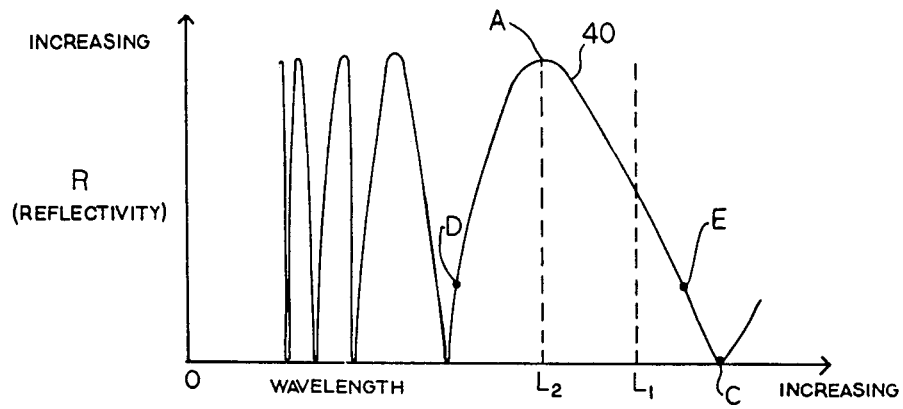
FIG. 2 is a graphic representation of a reflectivity curve for an optically resonant structure.

Referring now to FIG. 2, a typical reflectivity curve 40 of a parallel plane optically resonant structure 21 having a given set of physical characteristics is schematically illustrated. It is noted that reflectivity curve 40 is also typical of any other form of optically resonant structure 21 having a given set of physical characteristics which is not a parallel plane optically resonant structure. The reflectivity R of parallel plane optically resonant structure 21 is seen to be a periodic function of the wavelength of its input light - a common characteristic of optically resonant structures.

By examining the equations set forth above, it can be seen that, more generally, the reflectivity R of a parallel plane optically resonant structure 21 is a periodic function of the parameter group nt cos(phi)/lambda. For a parallel plane optically resonant structure 21, maximum reflectivities occur at nt cos(phi)/lambda=(2m+1)/4, while minimum reflectivities occur at nt cos(phi)/lambda=m/2; where m is the cycle number and is zero or a positive integer. By examining these two equations last mentioned, it is seen that adjacent maxima and minima (and vice versa) are separated such that the absolute value of parameter group nt cos(phi)/lambda changes by exactly ¼ between them.

By designing a parallel plane optically resonant structure 21 so that parameter group nt cos(phi)/lambda changes in response to the physical parameter being measured, it follows that, for any selected wavelength of input light, parallel plane optically resonant structure 21 will exhibit varying reflectivity as a function of the physical parameter being measured. It has been discovered that this varying reflectivity can be used in a novel way to detect and measure the physical parameter being measured as will be described in more detail subsequently.

The parameter group nt cos(phi)/lambda can be made to change in response to the physical parameter being measured if any of the optically sensitive physical characteristics of parallel plane optically resonant structure 21, such as its refractive index n or distance t, light refraction angle phi, and/or phase shift e, can be made to change as a function of the physical parameter being measured. In general, an optically sensitive physical characteristic of parallel plane optically resonant structure 21 is any of its physical characteristics which change its reflectivity as a function of the physical parameter being measured.

All of the preceeding remarks concerning parallel plane optically resonant structures 21 apply to all other forms of optically resonant structure 21 which are not parallel plane optically resonant structures. The remarks which follow apply to all forms of optically resonant structures 21, whether parallel plane or not.

Specific non-limiting examples of different spectral modulation sensors 22 having different optically resonant structures 21 in which at least one of their optically sensitive physical characteristics vary as a function of a physical parameter being measured are set forth in the following sections.

Figure 3:
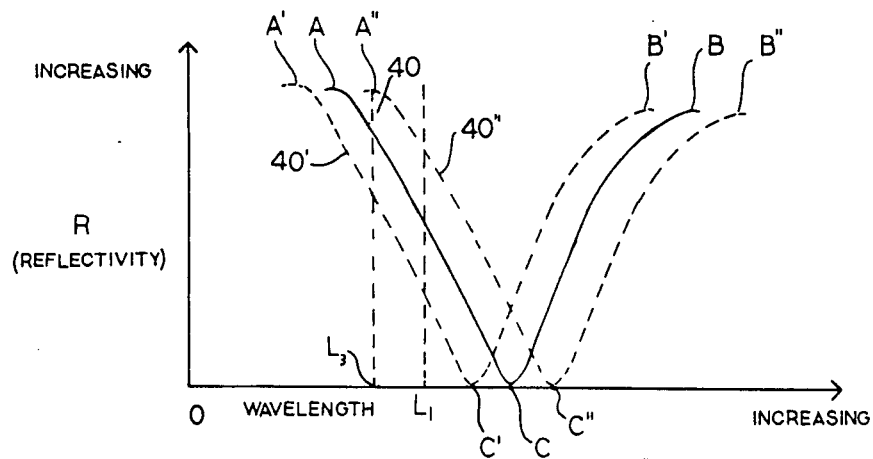
FIG. 3 shows a portion of the curve of FIG. 2 during operation of the first embodiment 1 of the optical measuring device.

Referring now to FIG. 3, an enlarged portion of reflectivity curve 40 is illustrated. FIG. 3 also illustrates, by way of non-limiting example, the effect on reflectivity curve 40 when any of the optically sensitive physical characteristics of its particular corresponding optically resonant structure 21 is altered.

Figure 8:
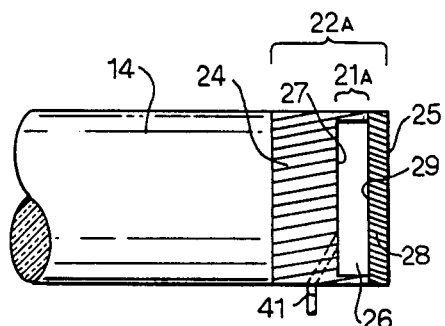

By way of non-limiting example, regarding optically resonant structure 21A of sensor 22A of FIG. 8, the optically sensitive physical characteristic may be the distance between the reflective bottom 27 of its cavity 26 and the inner surface 29 of its cover 28. For purposes of discussion, it may be assumed reflectivity curve 40 is also the reflectively curve for optically resonant structure 21A.

In FIG. 3, reflectivity curve 40 of optically resonant structure 21A is seen to be shifted to the left, with respect to any particular selected wavelength $L_1$ of input light from light source 10, to become reflectivity curve 40' when the distance between its reflective surfaces 27, 29 is reduced; and is seen to be shifted to the right with respect to $L_1$ to become reflectivity curve 40" when the distance between its reflective surfaces 27, 29 is increased.

It should be noted that FIG. 3 only schematically illustrates the actual effect since, as is discussed subsequently in more detail regarding sensor 22A and its optically resonant structure 21A, its reflective surfaces 27, 29, are not parallel during operation. In addition, as the reflectivity curve 40 is shifted left the bandwidth of each of its cycles decreases, while as it is shifted right, the bandwidth of each of its cycles increases.

However, in general, the reflectivity curve of any kind of optically resonant structure 21 shifts left and/or right with respect to wavelength $L_1$ as a function of any of its optically sensitive physical characteristics, such shifts being termed herein microshifts. An optically sensitive physical characteristic of any particular optically resonant structure 21 is defined as being any of its physical characteristics which cause such microshifts as a function of the physical parameter being measured. A resonance cycle of the reflectivity curve of any particular optically resonant structure 21 is defined a being one complete cycle on its reflectivity curve. There are, of course, a plurality of such resonance cycles on its reflectivity curve since a resonance cycle may start anywhere on its reflectivity curve.

By way of non-limiting example, a resonance cycle on reflectively curve 40 of any optically resonant structure 21 is AB, seen in FIG. 3.

It has been discovered that accurate measurements of the physical parameter being measured can be made using operating segment(s) of the reflectivity curve of the particular optically resonant structure 21, wherein the term operating segment is defined to be any portion of its reflectivity curve which is less than about one resonance cycle in length, and by using operating segment microshifts which are also less than about one resonance cycle in length, at the measuring input light wavelength(s). Since the reflectivity curve of any particular optically resonant structure 21 is cyclic, there are a plurality of such operating segments on it.

By way of non-limiting example, if the operating segment of reflectivity curve 40 of FIG. 3 were A"B" it is, of course, one resonance cycle in length. Further, if in response to the physical parameter begin measured operating segment A"B" were microshifted to the left until point B" intersected wavelength $L_3$, then the microshift of operating segment A"B" would be one resonance cycle in length.

By way of further non-limiting example with regard to the first embodiment 1 of the optical measuring device, let us choose to drive optically resonant structure 21 with a light source 10 which delivers monochromatic input light of a wavelength, such as $L_1$. Wavelength $L_1$ does not, of course, change if any of the optically sensitive physical characteristics of optically resonant structure 21 of sensor 22 are altered by the physical parameter being measured. Let us further choose AC to be the operating segment of resonance curve 40 for optically resonant structure 21 (see FIG. 3).

From an inspection of FIG. 3, it is seen that for any given intensity of input light of wavelength $L_1$ to sensor 22, the output intensity at wavelength $L_1$ from sensor 22's optically resonant structure 21 will be different when at least one of the optically sensitive physical characteristics of its optically resonant structure 21 are altered by the physical parameter being measured, as compared to when such optically sensitive physical characteristics of its optically resonant structure 21 are unaltered. This is due to the left and/or right microshifts of operating segment AC of optically resonant structure 21 (to become A'C' and A"C") in response to the physical parameter being measured.

Thus, sensor 22 is a spectral modulation sensor whose optically resonant structure 21 modulates its input light of wavelength $L_1$ as a function of the physical parameter being measured and produces modulated output light of wavelength $L_1$ which carries information regarding the physical parameter being measured. This information is converted by photodetector 30 and amplifier 34, as has been described, into an electrical output measuring signal carrying the same information.

Naturally, the wavelength(s) of input light from light source 10 which are actually utilized in measuring the physical parameter being measured, termed herein input measuring light, such as wavelength $L_1$, and/or the physical characteristics of the sensor's optically resonant structure 21 are selected such that such wavelength(s) of input measuring light fall at least substantially within the desired operating segment of its reflectivity curve. such as AC for example, over the desired operating range of values for the physical parameter being measured. Thus, as seen in FIG. 3, wavelength $L_1$ remained within operating segment AC, despite operating segment AC being microshifted by optically resonant structure 21 in response to the physical parameter being measured to become A'C' and/or A"C".

By suitably selecting the operating segment of optically resonant structure 21, as by a suitable selection of its optically sensitive physical characteristic(s), and/or by suitably selecting the measuring input light wavelength(s), it is possible to cause the output measuring signal of the optical measuring device 1 to vary either directly or inversely with changes in value of the physical parameter being measured. Causing the output measuring signal to vary inversely rather than directly may be done, for example, by using an operation segment having a negative slope, rather than a positive slope.

For greater sensitivity and/or for a wider potential range of values for which the physical parameter being measured can be measured by optically resonant structure 21, it is preferable that optically resonant structure 21 be designed such that changes in its output light due to its operating segment microshifts in response to the physical parameter being measured be maximized over the range of values of interest for the physical parameter being measured. This is achieved, for example, by suitable design of optically resonant structure 21, by suitable selection of a particular operating segment for it, and/or by suitable selection of the input measuring light's wavelength(s) and/or amplitude(s), to obtain an operating segment of greatest length which will yield unambiguous spectrally modulated output light from optically resonant structure 21 over the range of values of interest for the physical parameter being measured.

By way of non-limiting example, for a monochromatic measuring input light of wavelength $L_1$, changes in the output light of optically resonant structure 21 are maximized when its operating segment AC extends, as illustrated in FIG. 3, between any maxima and an adjacent minima (or vice versa) on its reflectivity curve 40, and when over the range of values of interest for the physical parameter being measured, the physical parameter being measured drives optically resonant structure 21 such that its operating segment AC is microshifted left and/or right sufficiently such that the entire operating segment AC intersects the input measuring light wavelength $L_1$, i.e., is microshifted a full half resonance cycle.

Operating segment(s) of reflectivity curve 40 for any particular optically resonant structure 21 which yield the greatest potential changes in the output light from optically resonant structure 21 due to its operating segment microshifts, at the wavelength(s) of the input measuring light, may vary according to the frequency and/or amplitude spectrum(s) of the input measuring light. On the other hand, it may be desirable to utilize only a portion of such operating segment(s) in order to improve the linearity of the output light from optically resonant structure 21, such as by using a particularly linear portion of it.

Naturally if the optically resonant structure 21 is driven by the physical parameter being measured such that its spectrally modulated output light signal does not bear a unique one-to-one relationship to the physical parameter being measured over the range of values of interest, then the output light signal may provide ambiguous information. By way of non-limiting example, for a monochromatic input measuring light $L_1$, this occurs when optically resonant structure 21 is driven by the physical parameter being measured such that its operating segment AC is micrshifted left and/or right such that it no longer intersects wavelength $L_1$.

In general, if it is found that the spectrally modulated output light from optically resonant structure 21 does not bear the desired one-to-one relationship, then selecting an input measuring light having different wavelength(s) and/or amplitude(s), selecting a different physical structure for optically resonant structure 21, and/or selecting different operating segment(s) of reflectivity curve 40 for optically resonant structure 21 until the desired unique one-to-one relationship is obtained can solve the problem. Further, proper calibration of the optically resonant structure 21, and/or using it only over its deigned range of values when measuring the physical parameter being measured is helpful.

For greater sensitivity, it is also desirable to increase the maximum to minimum (or vice versa) reflectivity difference of optically resonant structure 21, such as between AC in FIG. 3. This is done by coating at least one of its reflective surfaces 13, 15 with an appropriate thickness, say 100 to 200 Angstroms, for example, of a high refractive index transparent media that increases surfaces reflectivity, such as rutile, titanium dioxide, cubic zirconia or silicon.

Second Embodiment of the Optical Measuring Device

Figure 4:
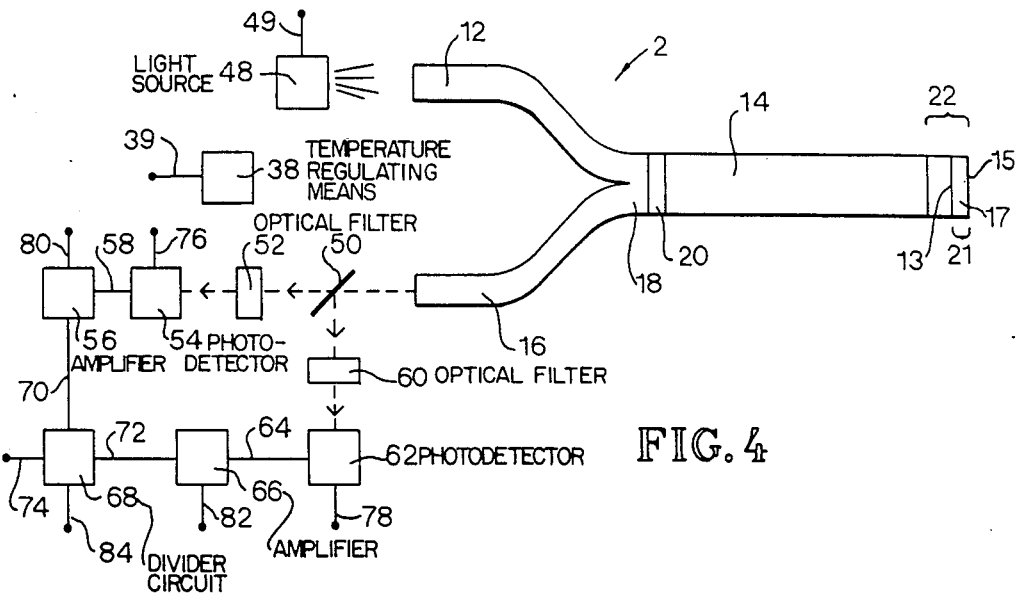
FIG. 4 is a schematic illustration of the second embodiment 2 of the optical measuring device.

The second embodiment 2 of the optical measuring device is schematically illustrated in FIG. 4. The first and second embodiments 1, 2 of the optical measuring device illustrated in FIGS. 1 and 4, respectively, are identical in theory, construction, use and all other respects, except for the differences which are discussed below. Accordingly, the same reference numerals used for certain parts of the first embodiment of FIG. 1 are used for the same parts in the same embodiment in FIG. 4, for clarity.

Turning now to the differences, in FIG. 4 light source 48 is now chosen to produce at least two light wavelengths and may be, by way of non-limiting example, a light emitting diode (LED) which emits a band of light wavelength(s) centered at approximately 810 nm, such as part #MFOE1202, made by the Motorola Co. Power for light source 48 is provided from any suitable source of electrical power through electrical connection means 49.

Spectrally modulated output light from output optical fiber 16 is directed onto a beam splitter 50 which divides it into two output light beams.

The first output light beam from beam splitter 50 passes through short pass optical filter 52, which transmits to an appreciable degree only light having a wavelength shorter than a given, preselected wavelength. The short wavelength output light band from filter 52 is converted to a first electrical signal by photodetector 54 and then conveyed to amplifier 56 by electrical connection means 58 to be amplified by amplifier 56. Said preselected wavelength may be, by way of non-limiting example, the wavelength of light from light source 48 of highest intensity, such as a wavelength of 810 nm, for the particular LED mentioned above.

The second output light beam from beam splitter 50 passes through long pass optical filter 60, which transmits to an appreciable degree only light having a wavelength longer than said given, preselected wavelength. The long wavelength output light band from filter 60 is converted to a second electrical signal by photodetector 62 and then conveyed by electrical connection means 64 to amplifier 66 to be amplified by amplifier 66. Amplifiers 56, 66 preferably amplify their respective signals to the same degree.

The amplified first and second electrical signals from amplifiers 56, 66 are conveyed to a divider circuit 68 by electrical connection means 70, 72. Divider circuit 68 takes the ratio thereof and provides an output measuring signal to electrical connection means 74. The output measuring signal carries information regarding the physical parameter being measured.

As has been mentioned, changes in the intensity of light source 48 and changes in light transmission intensity due to bending of optical fibers 12, 14, 16 and due to light loss in optical connector 20 may cause inaccuracies in the output measuring signal. However, it is noted that both said short and long wavelength output light bands from optical filters 52, 60 are affected equally by such changes. Accordingly, when their respective amplified first and second electrical signals are divided in divider circuit 68, such changes cancel each other out and have no effect on the output measuring signal from divider circuit 68. Such dividing of two signals is known as ratiometric signal processing.

Although the arrangement discussed above is preferred because it provides an optical measuring device with maximum sensitivity, it is possible to remove either filter 52 or filter 60 and still eliminate the inaccuracies in the output measuring signal discussed above. If short pass filter 52 is removed, then divider circuit 68 will take the ratio of the electrical signals from amplifiers 56, 66 corresponding to, respectively, the entire output light band from beam splitter 50 which falls on photodetector 54 and the long wavelength output light band from long pass filter 60. If long pass filter 60 is removed, then divider circuit 68 will take the ratio of the electrical signals from amplifiers 56, 66 corresponding to, respectively, the short wavelength output light band from short pass filter 52 and the entire output light band from beam splitter 50 which falls on photodetector 62. In either event such inaccuracies will again cancel each other out in divider circuit 68, in the manner discussed above, since all portions of the output light band from optical fiber 16 are affected equally by such inaccuracies.

Thus, it is within the scope of the present invention to eliminate the inaccuracies in the output measuring signal discussed above by having the divider circuit 68 take the ratio of the electrical signals corresponding to any two different portions of the output light from output optical fiber 16, even wherein one of said portions may be the entire output light from output optical fiber 16.

Power for photodetectors 54, 62, amplifiers 56, 66 and divider circuit 68 are provided by any suitable source of electrical power through electrical connection means 76, 78, 80, 82, 84, respectively.

Parts 50–84 form a detection means for converting the output light from the optically resonant structure 21 of sensor 22 into a useful electrical output measuring signal at electrical connection means 74.

Light source 48 and photodetectors 54, 62 are preferably housed in a housing of any suitable construction along with temperature regulating means 38, so temperature regulating means 38 can maintain them at a relatively uniform temperature to enhance the accuracy of the optical measuring device, as was discussed above regarding the first embodiment 1.

Theoretical Considerations for Second Embodiment of Optical Measuring Device

Now that the general construction and operation of the second embodiment 2 of the optical measuring device has been considered, the theory of operation of the second embodiment 2 as illustrated in FIG. 4 which is different from the theory of operation of the first embodiment 1 of the optical measuring device will now be addressed.

It will be recalled, regarding the first embodiment 1 of the optical measuring device of the present invention, wherein by way of non-limiting example the input measuring light was chosen to be monochromatic, that in order to eliminate ambiguity in the output light signal from spectral modulation sensor 22, at least two basic criteria had to be met. The two criteria for monochromatic input measuring light are that the maximum length and the maximum michroshifting of the operating segment of the reflectivity curve of optically resonant structure 21 could not exceed one-half of a resonant cycle.

In contrast, quite different constraints on these two basic criteria are found in the ratiometric second embodiment 2 of the optical measuring device, wherein at least two different input measuring light wavelengths to optically resonant structure 21 are used, and wherein ratiometric signal processing of the spectrally modulated output light from optically resonant structure 21 is also used. For the ratiometric second embodiment 2, it has been discovered that in order to eliminate ambiguity in the output light signal from spectral modulation sensor 22 the maximum length and the maximum michroshifting of the operating segment on its reflectivity curve both may approach but not exceed about one full resonance cycle.

This surprising result allows for a potentially wider dynamic response of the ratiometric second embodiment 2 as compared to the first embodiment 1. That is, the physical parameter being measured can drive its optically resonant structure 21 to modulate its input measuring light a greater amount without causing an ambiguity in the spectrally modulated output light signal from tis optically resonant structure 21. This permits either a desirable greater sensitivity of its optically resonant structure 21 over a given range of values of interest for the physical parameter being measured, or a desirable greater range of values for the physical parameter being measured which are capable of being measured by its optically resonant structure 21.

In practice, when the maximum length and microshifting of the operating segment of the reflectivity curve of its optically resonant structure 21 are desired, the operating segment is preferably centered around one of the reflectivity maxima on its reflectivity curve. However, if maximum response is not needed or desired, the operating segment need not be so centered. The length and microshifting of its operating segment may be selected to be considerably less than the maximum allowable so as to improve linearity in the output light signal of optically resonant structure 21.

It is noted that the wavelengths of the at least two input measuring wavelengths emitted by light source 48 of the ratiometric second embodiment 2 need no be close in wavelength. In fact, they could be chosen so as to fall on different operating segments of the reflectivity curve of optically resonant structure 21, which may even have different cycle numbers, m.

Thus, light source 48 could comprise at least two sources of monochromatic light such as lasers or laser diodes. Alternatively it could comprise one or more sources of a plurality of wavelengths, such as LED's or white light sources, along with suitable optical filters, as needed, to provide the at least two input measuring light wavelengths and/or wavelength bands.

However, it is preferred for simplicity that light source 48 be a single LED whose bandwidth, at the input measuring light wavelengths selected, is substantially less than the resonance cycle length of the reflectivity curve of optically resonant structure 21. Typical LED's available today meet this criteria since they have a bandwidth at one-half their peak intensity on the order of 10% of their wavelength of peak intensity, and thus have a total bandwidth substantially less than their wavelength of peak intensity.

Figure 5:
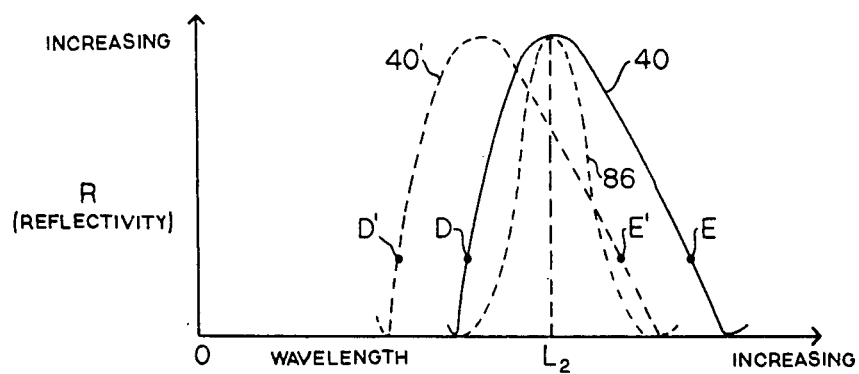
FIG. 5 shows a portion of the curve of FIG. 2 during operation of the second embodiment 2 of the optical measuring device.

Turning to FIG. 5, it schematically illustrates, by way of non-limiting example, in curve 86, the intensity of the output light of light source 48 as a function of wavelength, wherein light source 48 is a single LED. Wavelength $L_2$ is, by way of non-limiting example, selected to be at or near the most intense output wavelength of light from light source 48. Also schematically shown in FIG. 5 is an enlarged portion of reflectivity curve 40 taken from FIG. 2, which illustrates, by way of non-limiting example, operating segment DE on reflectivity curve 40 of optically resonant structure 21; and corresponding reflectivity curve 40' and operating segment D'E' which result from a shift of reflectivity curve 40 to the left due to the influence of the physical parameter being measured on one of the optically sensitive physical characteristics of optically resonant structure 21. Reflectivity curve 40 and its operating segment DE could also be shifted to the right in the same manner, but this is not illustrated in FIG. 5 for clarity.

Thus, as before regarding embodiment 1 of the optical measuring device, as the physical parameter being measured changes at least one of the optically sensitive physical characteristics of optically resonant structure 21 of sensor 22, the operating Segment DE of its reflectivity curve 40 will shift left and/or right in response thereto; such left and/or right shifts being termed operating segment microshifts, as mentioned earlier.

It has been discovered that such operating segment microshifts can be used to accurately measure the physical parameter being measured and can also be used to eliminated certain measurement inaccuracies mentioned previously, even when optically resonant structure 21 of sensor 22 is driven by at least two input measuring light wavelengths, such as curve 86, rather than being driven by monochromatic light, and even when ratiometric signal processing of the output light signal from optically resonant structure 21 is utilized.

Figure 6:
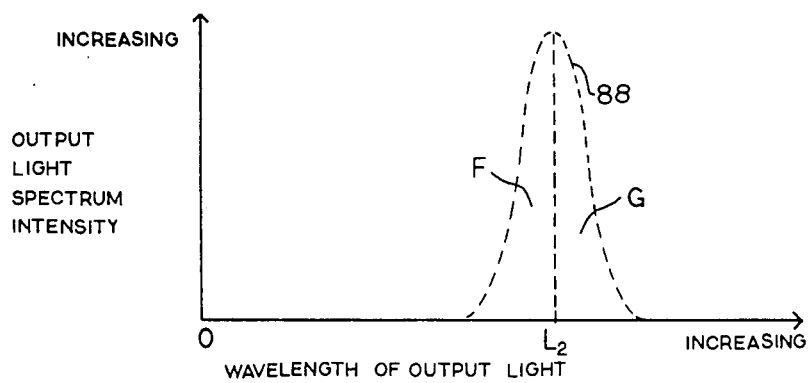
FIGS. 6 and 7 are graphic representations of the spectrally modulated output light of the second embodiment 2 of the optical measuring device.

Turning now to FIG. 6, it schematically illustrates, by way of non-limiting example, the output light spectrum intensity curve 88 of optically resonant structure 21 of sensor 22 when it is driven by a light source 48, having an output light curve 86 as shown in FIG. 5, and when optically resonant structure 21 has a reflectivity curve 40. It is noted that the areas F and G beneath optically resonant structure 21's output curve 88 to the left and right, respectively, of wavelength $L_2$ are about equal, with a ratio F/G about equal to one.

Figure 7:
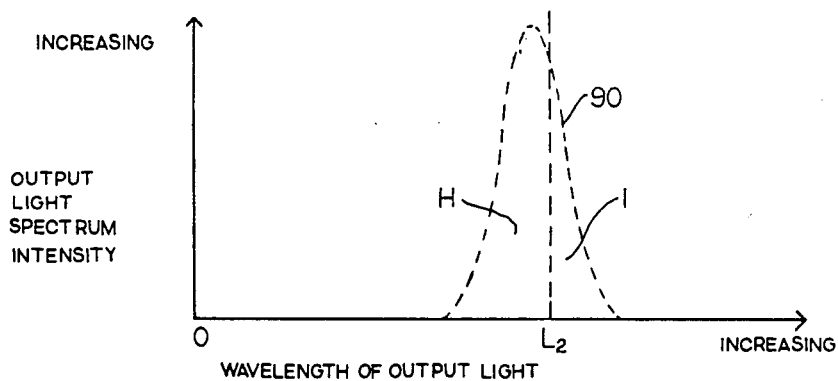

FIG. 7 schematically illustrates, by way of non-limiting example, optically resonant structure 21's output light spectrum intensity curve 90 when optically resonant structure 21 is driven by a light source 48 having an output light curve 86 as shown in FIG. 5, and when optically resonant structure 21 has a reflectivity curve 40'. It is noted that the areas H and I beneath optically resonant structure 21's output curve 90 to the left and right, respectively, of wavelength $L_2$ are now unequal, with a ratio H/I about equal to 2.

Thus, in general, over a certain range of values for the physical parameter being measured, the ratio of the left and right areas beneath the output light spectrum intensity curves of optically resonant structure 21, such as 88, 90, is a unique function of the left and/or right microshifts of the operating segment of optically resonant structure 21. Accordingly, such ratio provides an accurate measurement of the physical parameter being measured.

The segregation of the output light of optically resonant structure 21 into short and long wavelength portions to the left and right, respectively, of wavelength $L_2$ is performed in the manner previously discussed. The photodetectors 54, 62 integrate the output of the short and long wavelength portions, respectively; while the divider circuit 68 takes their ratio by taking the ratio of the first and second electrical signals from photodetectors 54, 62.

It is to be noted that the dividing of the output spectrum of optically resonant structure 21 into short and long wavelength portions and then taking their ratio accomplishes two objectives of the invention simultaneously. It not only provides an accurate output measuring signal; but also serves to cancel out certain inaccuracies to which the optical measuring device might otherwise be susceptible, as was discussed above.

First Embodiment 22A of Spectral Modulation Sensor (Pressure)

Figure 8A:
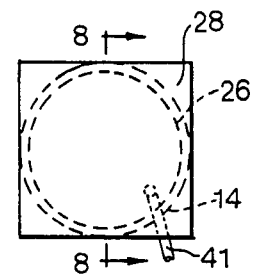
FIG. 8a is an elevation view of the right side of FIG. 8.

Turning now to FIGS. 8 and 8a, the first embodiment of a spectral modulation pressure sensor 22A having an optically resonant structure 21A is illustrated. Optically resonant structure 21A has the same theory, characteristics and operation as does optically resonant structure 21, except for any differences which are made apparent by the following.

Sensor 22A comprises a substrate 24, defining a cylindrical cavity 26, and has a cover 28 which covers cavity 26. Cavity 26 has a reflective bottom surface 27, while cover 28 has a reflective inner surface 29 and an outer surface 25. It is preferred, but not required, that the thickness of substrate 24 between the bottom 27 of its cavity 26 and the end of sensor optical fiber 14 be as was discussed regarding substrate 9 of sensor 22.

If an absolute pressure sensor 22A is desired, then cavity 26 is preferably evacuated, cover 28 providing it with a fluid tight seal. Alternatively, if a differential pressure sensor 22A is desired, cavity 26 could fluidly communicate with one source of pressure through optional conduit 41, while the other source of pressure would bear against outside surface 25 of cover 28. Naturally, optional conduit 41 is omitted if sensor 22A is to be an absolute pressure sensor.

Reflective surfaces 27 and 29 are preferably coated with about 100 to 200 Angstroms of a high refractive index transparent media, for the same reasons indicated regarding sensor 22.

Cavity 26, its reflective bottom 27, and reflective inner surface 29 of cover 28 form an optically resonant structure 21A. Since cavity 26 is preferably evacuated, the index of refraction of its contents, a vacuum, remains 1.000 at all times.

As alternative constructions for sensor 22A, it is of course possible to form its cavity 26 in its cover 28, rather than it its substrate 24; or even to form its cavity 26 partially in substrate 24 and partially in cover 28, without departing from the scope of the invention.

Figure 8B:
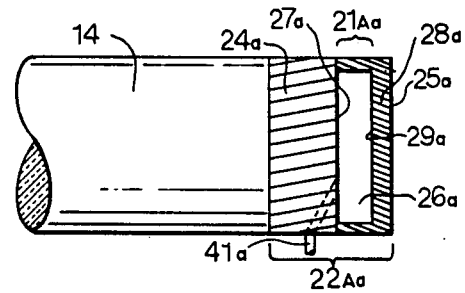
FIG. 8b is a schematic side elevation view showing a modified form of the first embodiment 22A of the spectral modulation sensor in a partial longitudinal cross section.

FIG. 8b illustrates a sensor 22Aa, which is essentially the same as sensor 22A, so similar parts have been given the same reference numerals with an "a" appended, for clarity. Sensor 22Aa has a cavity 26a formed in its cover 28a; cover 28a having an inner reflective surface 29a, and an outer surface 25a. Substrate 24a has a reflective surface 27a. Reflective surfaces 27a, 29a and cavity 26a form optically resonant structure 21Aa. If sensor 22Aa is to be a relative pressure sensor, conduit 41a is provided; while if sensor 22Aa is to be an absolute pressure sensor, conduit 41a is omitted and chamber 26a is evacuated. In either event, cover 28 is sealed to substrate 24a, like in sensor 22A.

The manner in which sensor 22A and its optically resonant structure 21A are made will now be described. From this description, the manner in which sensor 22Aa could be made will be apparent.

In order to reduce cost, it is preferred that a plurality of sensors 22A with their optically resonant structure 21A be produced simultaneously. By way of non-limiting example, it will be presumed that the optically resonant structures 21A have cavities 26 which are 200 microns in diameter and 1.27 microns deep.

The starting point is, for example, a 7740 Pyrex glass wafer 0.011±0.001 inches thick, three inches in diameter, and having both surfaces ground and polished to an optical finish, such as made by Vogelin Optical Co., Inc. of St. Paul, Minn. The glass wafer will form the substrates 24 of the sensors 22A.

The surfaces of the glass wafer are first cleaned by washing the glass wafer in hot, soapy water; rinsing it with clean water; etching and polishing it for one minute in a buffered HF solution composed of four parts of a mixture of 3 ml of water and 2 g $NH_4F$ plus 1 part 48% HF solution; rinsing it again, and then baking it at 300° for ½ hour.

Using a conventional vacuum deposition process, a layer of chrome 200 Angstroms thick is then deposited on the glass wafer. This chrome provides a good adhesion surface for the subsequent application of photoresist to the glass wafer.

Photorisist, such as Microposit 1400-27 photoresist made by the Shipley Company, located in Newton, Mass., is then spin coated on the chrome surface of the glass wafer at 3000 rpm; after which the coated glass wafer is baked at 90° C. for ½ hour.

Using conventional techniques, a photographic mask is then prepared having an array of circles of a diameter equal to the desired diameter of the cavities 26, here 200 microns for example. The mask is aligned with the photoresist coated surface of the glass wafer; and the mask and glass wafer assembly is then exposed. The exposed coated glass wafer is then developed with photoresist developer, such as Microdeposit 351CD-23 developer made by the Shipley Company; rinsed in water; and dried.

As a result, unprotected circles 200 microns in diameter in the photoresist are left on the glass wafer. The chrome within the unprotected circles in the photoresist is lifted off with a chrome etch solution composed of one part HCL and one part glycerine, leaving circles of unprotected glass 200 microns in diameter on the surface of the glass wafer.

The circles of unprotected glass on the glass wafer are then etched for about 20 minutes at 69° F. with said buffered HF solution to produce the cavities 26 which are 1.27 microns deep, for example.

It has been discovered that even though the bottoms 27 of the cavities 26 are formed by chemical etching, they are still flat enough to form an adequate reflective surface 27 for the sensor's optically resonant structure 21A.

Using conventional vacuum deposition techniques, a layer of titanium dioxide 200 Angstroms thick is then deposited on the bottom 27 of each cavity 26 to increase the reflectivity of the bottoms 27 of the cavities 26. This increases the intensity of the modulation of the output light of the optically resonant structures 21A as discussed earlier.

Then the remaining photoresist and chrome on the glass wafer are removed with acetone and with said chrome etch solution, respectively; after which the glass wafer is washed in water and air dried.

Getter Rings for First Embodiment 22A of Spectral Modulation Sensor

When pressure is the physical parameter which the first embodiment 22A of the spectral modulation sensor 22 is designed to detect, it is preferred that cavity 26 of its optically resonant structure 21A be evacuated. This is because evacuating the cavity 26 renders the optically resonant structure 21A immune to errors that would otherwise arise due to changes in temperature if cavity 26 contained some media which significantly expanded or contracted in response to changes in temperature.

Naturally, as mentioned previously, if a differential pressure sensor 22A is desired cavity 26 need not be evacuated.

Although there are many ways in which the cavity 26 can be evacuated, it is preferred to use a getter structure in the form of a ring of deposited layers of chrome and iron in the bottom of each cavity 26 to absorb residual gasses or subsequent outgassing in cavity 26 after the initial evacuation of cavity 26 is performed.

The getter rings for cavities 26 in the glass wafer are prepared as follows. First the glass wafer which has been prepared as described above, is baked at 125° C. for ½ hour; spun coated as before with photoresist; and baked again at 90° C. for ½ hour.

Then using conventional techniques, a second photographic mask is prepared having an array of donut shaped masks. Since the cavities 26 are 200 microns in diameter, for example, the corresponding donut shaped mask for each cavity 26 would have an inner diameter of 140 microns and an outer diameter of 190 microns, for example.

Then, the donut shaped masks on the second photographic mask are aligned with the cavities 26 in the glass wafer; and the mask and glass wafer assembly is exposed, as before. The glass wafer is then, as before, developed and rinsed; and then baked at 90° C. for ½ hour. This leaves an unprotected donut shaped hole in the photoresist in the bottom 27 of each cavity 26 having an inner diameter of 140 microns and an outer diameter of 190 microns.

Next, using conventional vacuum deposition techniques, a layer of chrome 200 Angstroms thick is deposited on the entire glass wafer, followed by a layer of iron 800 Angstroms thick being deposited on the layer of chrome. The chrome helps the iron, which is the actual getter material, to adhere to the glass wafer. Then the glass wafer is placed in acetone and agitated with ultrasound. This removes the remaining photoresist and also removes the chrome and iron, but only the chrome and iron which was over said remaining portions of photoresist. Finally, the glass wafer is washed with detergent; rinsed with water; and dried.

The getter structure thus left will comprise a donut shaped ring of the deposited chrome and iron layers with an inner diameter of 140 microns and an outer diameter of 190 microns centered in the bottom 27 of each cavity 26. Note getter rings leave a clear central portion 140 microns in diameter in the bottom of each cavity 26 through which light can pass. As discussed below, after covers 28 are bonded to cavities 26, the getter rings remove gases from cavities 26.

Bonding Covers Over the Cavities for First Embodiment 22A of Spectral Modulation Sensor The covers 28 for cavities 26 of sensors 22A will be formed, for example, from a silicon wafer 3 inches in diameter, about 0.018 inches thick, and etch stopped with $10^{20}$ boron atoms/cc$^3$ at a depth of 4.0 microns, as sold by Diffusion Technology, Inc. of Milipitas, Calif. 95035. Thus, the silicon wafer comprises an etch stopped layer 4.0 microns thick supported by a silicon substrate of much greater thickness.

In the bonding procedure, first the etch stopped side of the silicon wafer has a layer of silicon dioxide about 200 Angstroms thick formed on it by baking the silicon wafer in an over at 900° C. for one hour, in order to increase the subsequent adhesion of the glass wafer to it, as described subsequently.

Next, the glass and silicon wafers, which have been prepared as previously described, are cleaned with warm soapy water, cleaned in an ultrasound bath for about 15 minutes, rinsed with water, rinsed with alcohol, cleaned with alcohol, rinsed with alcohol and finally air dried. The etch stopped layer of the silicon wafer is then placed on and aligned with the surface of the glass wafer which bears the cavities 26 to form a silicon and glass wafer sandwich.

Then the silicon and glass wafers are bonded together by first being placed in a conventional vacuum chamber with a positive electrode in electrical contact with the outer surface of the silicon wafer and with a negative electrode in electrical contact with the outer surface of the glass wafer; after which the vacuum chamber is evacuated to about $6 \times 10^{-6}$ torr for 1 hour.

The silicon and glass wafer sandwich is then heated by a heater in the vacuum chamber to, and maintained at 500° C. While the assembly is at this temperature, a bonding voltage is applied to the positive and negative electrodes. The bonding voltage is ramped from 0–800 VDC, maintained at 800 VDC for about 8–10 minutes until the bonding current is stabilized, and then turned off. At this time the silicon and glass wafers are now bonded together with a fluid tight seal, the silicon dioxide layer on the silicon wafer aiding in the bonding process.

Then the temperature of the now bonded silicon and glass wafer sandwich is continued to be maintained at 500° C. for one-half hour to activate the getter rings in the bottoms 27 of cavities 26. As has been mentioned, the function of the getter rings is to remove any residual gasses or subsequent outgassing in cavities 26 after the bonding of the silicon and glass wafer sandwich, thereby producing a very good vacuum in cavities 26.

Next the heater in the vacuum chamber is turned off and when the silicon and glass wafer sandwich has cooled to about 300° C., the vacuum in the vacuum chamber is released. The bonded silicon and glass wafer sandwich is removed from the vacuum chamber when it has cooled to about 200° C.

Then 70% to 80% of the thickness of the silicon substrate of the silicon wafer in the bonded silicon and glass wafer sandwich is removed by mechanical polishing. Next an EDP etchant solution is prepared composed of 8 ml water, 17 ml ethylenediamine, and 3 g pyrocatechol. The EDP etchant solution is heated to approximately 115° C. and used to chemically etch the pure silicon substrate away, leaving only its etch stopped layer, about 4.0 microns thick, which is bonded to the glass wafer and which forms the covers 28 for cavities 26. The 4.0 microns thickness is determined by periodically checking the thickness of the silicon remaining during the etching process, such as by measuring light transmission through the silicon.

Adding Light Absorbing Coating to Outside of Covers for First Embodiment 22A of Spectral Modulation Sensor By way of non-limiting example, after the bonded silicon and glass wafer sandwich is prepared as described above, a light absorbing and/or reflecting coating may then be added to the outer surface 25 of the etch stopped layer which forms the covers 28 for cavities 26. The light absorbing and/or reflecting coating may be formed by using conventional vacuum deposition techniques to deposit two or more alternating layers of chrome and silicon on the outer surface 25 of the etch stopped layer of the silicon and glass wafer sandwich. The chrome is deposited first; with each layer of chrome and silicon being about 25 and 100 Angstroms thick, respectively. The purpose of the light absorbing and/or reflecting coating is to prevent external light from entering optically resonant structure 21A through its cover 28, and to prevent light transmitted through optically resonant structure 21A into cover 28 from reentering the optically resonant structure 21A from cover 28.

Dicing Wafer Sandwich Into Individual Sensors and Mounting Sensors for First Embodiment 22A of Spectral Modulation Sensor After the wafer sandwich is prepared as described above, it is diced or divided into individual spectral modulation sensors 22A using conventional techniques.

In order to mount sensor 22A to the free end of sensor optical fiber 14, the free end of sensor optical fiber 14 is first cleaved, or ground and polished to be optically flat. Then the sensor 22A is mounted to the free end of sensor optical fiber 14 by using an adhesive having a suitable index of refraction, such as adhesive #415 made by the American Chemical and Engineering Company of Torrington, Conn. Preferably, the index of refraction of such adhesive is one which matches the indices of refraction of sensor optical fiber 14 and substrate 24 of sensor 22A as closely as possible.

Calibration of First Embodiment 22A of Spectral Modulation Sensor

After sensor 22A is mounted on the end of sensor optical fiber 14 of either the first or second embodiment 1, 2 of the optical measuring device, sensor 22A can be easily calibrated by subjecting it to a series of known pressures and noting the corresponding outputs at output terminal 36 or 74.

Operation and Theoretical Considerations for First Embodiment 22A of Spectral Modulation Sensor The first embodiment 22A of the spectral modulation sensor which is shown in FIGS. 8, 8a and 8b is useable with either embodiment 1 or 2 of the optical measuring device to measure pressure by mounting it, as has been described, to the free end of sensor optical fiber 14 in lieu of spectral modulation sensor 22 seen in FIGS. 1 and 4.

Sensor 22A's operation as an absolute pressure sensor will first be described. When sensor 22A is subjected to an external pressure, cover 28 over evacuated cavity 26 will be bowed inwardly towards the reflective bottom 27 of cavity 26 to a greater or lesser degree depending on the amount of external pressure. As the external pressure on cover 28 increases, such bowing increases; and as the external pressure decreases, the bowing decreases and becomes zero when the external pressure is zero.

Accordingly, as the external pressure on cover 28 increases, the distance between reflective surfaces 27, 29 of optically resonant structure 21A decreases. Conversely, as the external pressure on cover 28 decreases, the distance between reflective surfaces 27, 29 of optically resonant structure 21A increases and becomes a maximum when the external pressure is zero.

When sensor 22A is operated as a differential pressure sensor, one source of pressure is fluidly communicated to cavity 26, such as through conduit 40, while surface 25 of cover 28 is exposed to a second source of pressure. When the pressure on surface 25 exceeds that within cavity 26, operation of differential sensor 22A is similar to that described above regarding absolute pressure sensor 22A. That is, cover 28 will bow inwardly towards the reflective bottom 27 of cavity 26 when pressure on surface 25 of cover 28 exceeds that within cavity 26, the amount of bowing depending on the pressure differential, and will not bow at all when the pressure differential is zero. However, when the pressure within cavity 26 is greater than that on surface 25 of cover 26 cover 28 will bow outwardly, the amount of bowing again depending on the pressure differential.

For sensor 22A, whether used as an absolute or differential pressure sensor, bowing of cover 28 in response to pressure causes changes in the distance between reflective surfaces 27, 29 of optically resonant structure 21A which, in turn, produce corresponding microshifts in the reflectivity curve and operating segment(s) of optically resonant structure 21A as a function of the pressure to which sensor 22A is subjected, much in the manner previously described regarding sensor 22. As a result, output light from sensor 22A is spectrally modulated as a function of the pressure to which sensor 22A is subjected and carries accurate information regarding such pressure.

It is worthy to note that an ideal optically resonant structure comprises spaced apart reflective surfaces which are parallel. But from the above it is seen that optically resonant structure 21A is far from ideal, because for any given absolute or differential pressure being detected reflective surface 29 of cover 28 is bowed inwardly or outwardly a corresponding amount. Since bottom reflective surface 27 of cavity 26 is flat to within about 150 Angstroms or to within about 1/20th of the average wavelength of input measuring light to sensor 22A, bowed reflective surface 29 is not parallel to reflective surface 27. Instead, the distance between reflective surfaces 27, 29 varies with radial position from the center of cavity 26 and cover 28. Accordingly, light reflected from optically resonant structure 21A will be composed of a complex mixture of light which has been spectrally modulated to a greater or lesser degree according to the radial position from which each particular light ray has been reflected from reflective surface 29.

Nevertheless, it has been discovered that accurate measurements of pressure can be made by sensor 22A even though when reflective surface 29 of its optically resonant structure 21A is bowed by the sensed pressure it is not parallel to the reflective bottom 27 of cavity 26.

Figure 9:
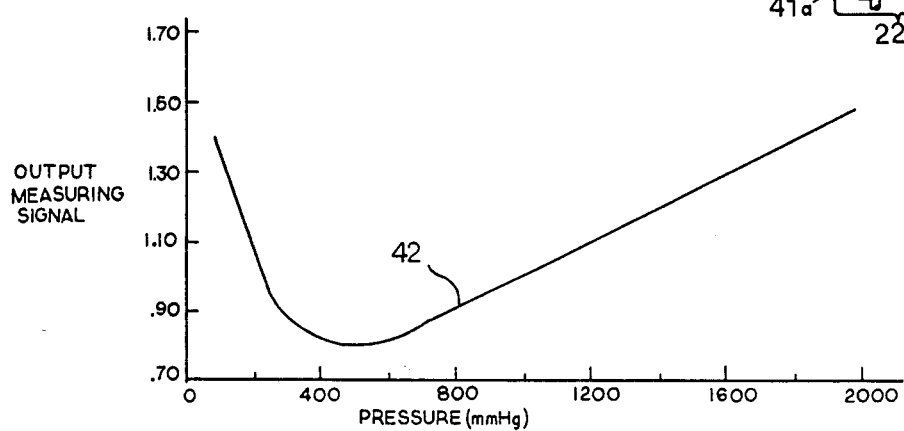
FIG. 9 is a graphic representation of the output from the spectral modulation sensor 22A as used with the second embodiment 2 of the optical measuring device.

FIG. 9 illustrates graphically in curve 42 a measurement of absolute pressure by a sensor 22A when constructed in accordance with the teaching herein, and when used with embodiment 2 of the optical measuring device. The output measuring signal is measured in arbitrary units.

Second Embodiment 22B of Spectral Modulation Sensor (Gas Density)

It should be noted that sensor 22A is easily modified to form the gas density sensor 22B seen in FIGS. 10 and 10a. Gas density sensor 22B is the same in all respects as pressure sensor 22A, except for those differences which will be made apparent from the discussion below, so like parts have been given the same reference numerals for clarity. In sensor 22B a small aperture 19 or 23 has been provided, as shown, in either it cover 28 or its substrate 24, respectively, which permits the gas to be sensed to enter its cavity 26. In such event, its optically resonant structure 21B would comprise reflective surfaces 27, 29 and the gas within cavity 26. In general, the index of refraction of the gas in cavity 26 is a function of its density, with changes in the density of the gas in cavity 26 causing a corresponding change in such gas's index of refraction.

Such changes in the index of refraction of optically resonant structure 21B produce corresponding microshifts in the reflectivity curve and operating segment(s) of optically resonant structure 21B as a function of the density of the gas in cavity 26. As a result, output light from sensor 22B is spectrally modulated by optically resonant structure 21B as a function of the density of the gas in cavity 26, and carries accurate information regarding such density.

The distance between reflective surfaces 27, 29 would not be expected to change during use of sensor 22B since the sensor's internal and external pressure would equalize through aperture 19 or 23. Naturally, since gas density sensor 22B is not evacuated, no getter ring in its cavity 26 is needed. Sensor 22B is useable with either embodiment 1 or 2 of the optical measuring device as was described regarding sensor 22A.

Third Embodiment 22C of Spectral Modulation Sensor (Temperature)

Referring now to FIGS. 11 and 11a, the third embodiment 22C of spectral modulation sensor 22 is a temperature sensor 22C having an optional substrate 92 with a peripheral edge 99. Substrate 92 supports a layer of sensitive media 94 having reflective inner and outer surfaces 96, 98, and a peripheral edge 100. Substrate 92 is similar in all respects to substrate 9 of sensor 22 discussed previously. Sensitive media 94, with its reflective inner and outer surfaces 96, 98 forms an optically resonant structure 21C.

It is preferred that external light does not enter optically resonant structure 21C. Accordingly, the external surface 98 of sensitive media 94 and peripheral edges 99, 100 may have a light absorbing and/or reflecting coating deposited on them. Alternatively, a light blocking housing, such as made from metal or some other heat conducting, light blocking material, could be secured in place over sensor 22C and the end portion of sensor optical fiber 14 to exclude undesired external light.

Sensor 22C is useable with either embodiment 1 or 2 of the optical measuring device to measure temperature by mounting it to the free end of sensor optical fiber 14, in the manner indicated regarding sensor 22A, in lieu of sensor 22 seen in FIGS. 1 and 4. Alternatively, sensor 22C could be mounted to sensor optical fiber 14 reversed, such that sensitive media 94, rather than substrate 92, contacts sensor optical fiber 14. Alternatively, sensor 22C may not include substrate 92 at all, in which case sensitive media 94 is mounted directly to the free end of sensor optical fiber 14.

By way of non-limiting example, two forms of temperature sensor 22C will be discussed.

In the first form of temperature sensor 22C, sensitive media 94 is a layer of silicon 0.7 microns thick, and preferably having both inner and outer surfaces optically flat to within 1/20th of the average wavelength of the input light to sensor 22C. Substrate 92 is a layer of 7740 Pyrex glass.

Preferably a plurality of such sensors 22C are made simultaneously be selecting wafers of 7740 Pyrex glass and silicon; bonding them together; polishing and etching the silicon wafer to the desired thickness; applying the light absorbing and/or light reflective coating; and dicing the wafer sandwich in a manner similar to that described earlier regarding pressure sensor 22A.

In use, light entering the inner surface 96 of optically resonant structure 21C from sensor optical fiber 14 is internally reflected between its reflective surfaces 96, 98. As the temperature of silicon layer 94 changes, the index of refraction of the silicon layer 94 also changes.

Such changes in the index of refraction of optically resonant structure 21C produce corresponding microshifts in the reflectivity curve and operating segment(s) of optically resonant structure 21C as a function of the temperature to which sensor 22C is subjected, much in the manner previously described regarding sensor 22. As a result, output light from sensor 22C is spectrally modulated by its optically resonant structure 21C as a function of the temperature to which sensor 22C is subjected and carries accurate information regarding such temperature.

In lieu of silicon, sensitive media 94 could be made from any other material having an index of refraction which varies significantly over the measurement temperature range of interest, such as semiconductor materials besides silicon, certain glasses and plastic films.

The second form of temperature sensor 22C is the same in all respects as the first form just described, except for the differences which will become apparent from the following discussion.

In the second form, sensitive media 94 comprises a layer of material preferably having a relatively high temperature expansion coefficient, such as polyvinyl chloride or polyethylene. Substrate 92 may, again, be a layer of 7740 Pyrex glass.

In use, light entering the inner surface 96 of optically resonant structure 21C from sensor optical fiber 14 is internally reflected between its reflective surfaces 96, 98. As the temperature of sensitive media 94 changes, it expands or contracts, thereby changing the distance between reflective surfaces 96, 98.

Such changes in the distance between reflective surfaces 96, 98 of optically resonant structure 21C produce corresponding microshifts in the reflectivity curve and operating segment(s) of optically resonant structure 21C as a function of the temperature to which sensor 22C is subjected, much in the manner previously described regarding sensor 22. As a result, output light from sensor 22C is spectrally modulated by its optically resonant structure 21C as a function of the temperature to which sensor 22C is subjected and carries accurate information regarding such temperature.

Fourth Embodiment of Spectral Modulation Sensor (pH) (Modified Form of Temperature Sensor 22C)

It should be noted that temperature sensor 22C may be modified to form a pH sensor. This is done by making sensitive media 94 from a glass or other material which will contract or swell in response to changes in pH. It is noted that pH sensor 22C is identical to temperature sensor 22C discussed above in all regard, except for this difference and the differences made apparent by the discussion which follows.

In pH sensor 22C, sensitive media 94 may be made form type 015 pH sensitive glass made by Corning Glass Co., located in Corning, N.Y. The pH sensitive glass layer 94 and its reflective surfaces 96, 98 form optically resonant structure 21C.

In operation, as pH sensitive glass layer 94 contracts or swells in response to changes in pH, the reflective surfaces 96, 98 of its optically resonant structure 21C will move closer together or farther apart in response to changes in pH. Such changes in the distance separating reflective surfaces 96, 98 produce corresponding microshifts in the reflectivity curve and operating segment(s) of optically resonant structure 21C as a function of the pH to which pH sensor 22C is subjected, much in the manner previously described regarding sensors 22 and 22A. As a result, output light from pH sensor 22C is spectrally modulated by its optically resonant structure 21C as a function of the pH to which pH sensor 22C is subjected and carries accurate information regarding such pH.

Fifth Embodiment 22D of Spectral Modulation Sensor (Chemical)

Turning now to FIGS. 12 and 12a, a fifth embodiment 22D of spectral modulation sensor 22 is illustrated, having a substrate 104, a cavity 106 with a reflective bottom 107, and a cover 108 with a reflective inner surface 112. Alternatively, cavity 106 could be formed in cover 108, or in both cover 108 and substrate 104, as was described regarding sensor 22A, see sensor 22Aa of FIG. 8b. Cover 108 is selected to be permeable to the physical parameter being measured, while cavity 106 is filled with a sensitive media 110 whose physical properties change in response to the physical parameter being measured. Optically resonant structure 21D of sensor 22D comprises reflective surfaces 107, 112 and sensitive media 110. Spectral modulation sensor 22D is secured to the end of sensor optical fiber 14 as was sensor 22A, and is useable with either embodiment 1 or 2 of the optical measuring device to measure sensed chemical species, i.e. atoms, molecules and ions.

By way of non-limiting example, cover 108 may be made of a metal or other material vapor deposited in a pattern with holes on the outer surface of sensitive media 110, microporous glass, or a material such as silicon, with a pattern of holes etched, or otherwise fabricated, through it to allow communication between the sensitive media 110 and the external environment. Alternatively, cover 108 may be made of an ion or gas selective membrane, such as a permeable or semipermeable membrane, and may be, by way of non-limiting example, a polymeric material such as polyethylene, cellulose acetate, or Silastic (manufactured by Dow Corning Corp.). Such an alternative cover 108 may, by way of non-limiting example, be formed by spin or dip coating or vacuum depositing such membrane on substrate 104 and sensitive media 110. Substrate 104 and cavity 106 may be fabricated as were substrate 24 and cavity 26 of sensor 22A. The thickness and presence of substrate 104 between reflective surface 107 and the end of sensor optical fiber 14 is subject to the same parameters described regarding substrate 9 of sensor 22.

In a first instance, sensitive media 110 is chosen such that it contracts and/or swells in response to the concentration or presence of the physical parameter being measured, namely sensed chemical species such as pH, $pO_2$, $pCO_2$, certain ions, etc. In this instance, cover 108 may be bonded to substrate 104 and be chosen to be flexible.

In operation, such contraction or swelling of sensitive media 110 will cause cover 108 to bow inwardly and/or outwardly to a greater or lesser degree. As a result, optically resonant structure 21D will spectrally modulate the output light from sensor 22D as a function of the concentration or the presence of the sensed chemical species, much as was described regarding pressure sensor 22A. As a result, spectrally modulated output light from optically resonant structure 21D carries information as to the concentration or presence of the sensed chemical species.

Alternatively, in this first instance, cover 108 need not be bonded to substrate 104 and may extend over only the outer surface of sensitive media 110. Here again, optically resonant structure 21D comprises reflective surfaces 107, 112, and media 110. In this event contraction or swelling of sensitive media 110 may not bow cover 108 and its reflective surface 112, but may instead displace cover 108 and its reflective surface 112 closer to or further away from reflective surface 107 in a more or less parallel fashion, thereby still spectrally modulating the output light from sensor 22D as a function of the sensed chemical species, much in the same manner described regarding sensor 22 and pressure sensor 22A.

Alternatively, in this first instance, cover 108 may be eliminated and the outer surface of sensitive media 110 treated, if desired, to increase its reflectivity. In such event, optically resonant structure 21D would comprise sensitive media 110, its outer surface and surface 107. It would spectrally modulate the output light from sensor 2D when contraction or swelling of sensitive media 110 moves its outer surface and surface 107 closer together or further apart, much in the same manner described regarding sensors 22 and 22A.

Alternatively, in this first instance, with reference to FIGS. 11 and 11a, a flat substrate 92 could be used instead of substrate 104 and have placed on it a thin coating of sensitive media 110, in lieu of sensitive media 94, such as by vapor deposition or spin coating. Naturally, substrate 104 could be eliminated, as discussed regarding substrate 9 of sensor 22A, and sensitive media 110 could be placed directly on the end of sensor optical fiber 14. Surface reflectivity of outer surface of sensitive media 110 may be enhanced by the use of any conventional technique. In this alternative form, optically resonant structure 21D would comprise the layer of sensitive media 110 and its inner and outer reflective surfaces corresponding to reflective surfaces 96, 98 of sensor 22C. Spectral modulation results when contraction or swelling of sensitive media 110 moves its reflective surfaces closer together or further apart, much in the manner described regarding sensor 22 and pressure sensor 22A.

By way of non-limiting example regarding the first instance, sensitive media 110 is a silicone rubber made by Dow Corning Corp. located in Midland, Mich. Cavity 106 is filled with the silicone rubber by first evacuating cavity 106 and then allowing prepolymerized but unset silicone rubber to flow into cavity 106.

As is known, when silicone rubber is exposed to the physical parameter here being measured, namely certain chemical species, particularly solvents such as ethyl ether or chloroform, the silicone rubber will swell and/or contract, depending on the concentration of the sensed chemical species.

In a second instance, sensitive media 110 is chosen such that its index of refraction changes as a function of the concentration and/or presence of the physical parameter being measured, namely sensed chemical species such as pH, $pO_2$, $pCO_2$, certain ions, etc. Cover 108 is preferably selected such that it will not deflect significantly during use of such a sensor 22D.

In operation, such changes in the index of refraction of sensitive media 110 cause optically resonant structure 21D to spectrally modulate the output light form sensor 22D as a function of the concentration or presence of the sensed chemical species, much as was described regarding sensor 22C. As a result, spectrally modulated output light from optically resonant structure 21D carries information as to the concentration or presence of the sensed chemical species.

Alternatively, in this second instance, cover 108 may be eliminated, and the outer surface of its sensitive media treated, if desired, to increase its reflectivity. In such event, optically resonant structure 21D comprises sensitive media 110 and its inner and outer reflective surfaces. It would spectrally modulate the output light from sensor 22D when the index of refraction of sensitive media 110 changed, much in the same manner described retarding sensor 22C.

Alternatively, in this second instance, with reference to FIGS. 11 and 11a, a flat substrate 92 could be used instead of substrate 104 and have placed on it a thin coating of sensitive media 110, in lieu of sensitive media 94, such as by vapor deposition, or spin or dip coating. Naturally, substrate 104 could be eliminated, as discussed regarding substrate 9 of sensor 22A, and sensitive media 110 could be placed directly on the end of sensor optical fiber 14. Surface reflectivity of outer surface of sensitive media 110 may be enhanced by the use of any conventional technique. In this alternative form, optically resonant structure 21D would comprise the layer of sensitive media 110 and its inner and outer reflective surfaces corresponding to reflective surfaces 96, 98 of sensor 22C. Spectral modulation results when the index of refraction of sensitive media 110 changes as a function of the concentration or presence of the sensed chemical species, much in the manner as described regarding temperature sensor 22C.

By way of non-limiting example regarding the second instance, sensitive media 110 is selected to be a polymeric media, such as polystyrene that has been copolymerized with an indicator substance such as methylene blue.

In use, the sensed chemical species will cause changes in the indicator substance in polymeric media 110, by interacting with such indicator substance, thereby changing the index of refraction of polymeric media 110. When the sensor 22D is constructed as described in this example it will measure hydrogen ion or oxygen gas concentration.

In a third instance, sensitive media 110 is chosen such that it is a first solvent or a first solvent/solute solution, and cover 108 is bonded to substrate 104. In use, sensor 22D is immersed in a second solvent or second solvent/solute solution which need not necessarily be the same as the first solvent or first solvent/solute solution. The sensed chemical species is at least one of the components of the solutes in the first and/or second solvent/solute solutions. Cover 108 is a membrane which is semipermeable to at least one of the first and/or second solvents and/or at least one of the components of the solutes in the first and/or second solvent/solute solutions.

In use, differences in the ion concentration across cover 108 will cause an osmotic pressure difference that, in turn, causes cover 108 to bow inwardly and/or outwardly as a function of the sensed chemical species. Such bowing of cover 108 will cause optically resonant structure 21D to spectrally modulate the output light from sensor 22D as a function of the concentration or presence of the sensed chemical species, much as was described regarding sensor 22A. As a result, spectrally modulated output light from optically resonant structure 21D carries information as to the concentration or presence of the sensed chemical species.

By way of non-limiting example regarding the third instance, sensitive media 110 is an aqueous solution of a salt, while semipermeable cover 108 is made from Nafion, which is a sulfonated fluorocarbon compound made by Dow Chemical Co. of Midland, Mich. A sensor 22D with this construction will detect the concentration or presence or various dissolved salts in water.

Transmission Embodiments of the Optical Measuring Device

Figure 14:
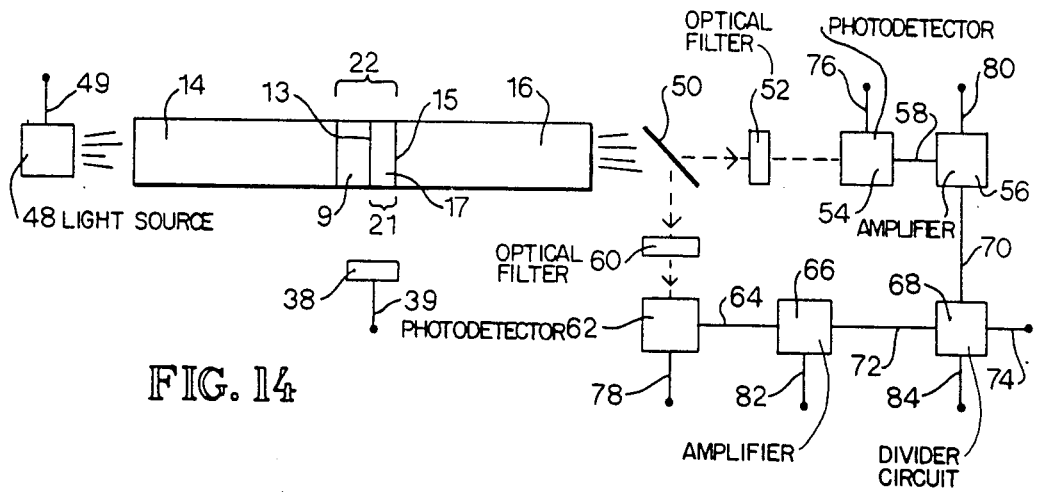
FIG. 14 is a schematic illustration of the fourth embodiment of the optical measuring device.

Referring now to FIGS. 13 and 14, the third and forth embodiments of the optical measuring device are illustrated. They are the same, respectively, as the first and second embodiments of the optical measuring device illustrated in FIGS. 1 and 4, except for differences which will be made apparent from the following discussion, so the same reference numerals for the same parts are used in the corresponding figures.

In FIGS. 13 and 14 separate input and output optical fibers 14, 16 are used with spectral modulation sensor 22, as seen. The input measuring light from light source 10 or 48 is conveyed by input optical fiber 14 to spectral modulation sensor 22 where it is spectrally modulated by optically resonant structure 21 as a function of the physical parameter being measured. Spectrally modulated output light from sensor 22 is conveyed by output optical fiber 16 to the detection means where it is converted into an electrical output measuring signal at output terminals 36, 74 in the manner previously discussed regarding FIGS. 1 and 4.

FIGS. 13 and 14 illustrate transmission embodiments of the optical measuring device since the input measuring light to sensor 22 is spectrally modulated as it passes through optically resonant structure 21 in sensor 22, rather than being spectrally modulated as it is reflected from optically resonant structure 21 in sensor 22 as was the case regarding the reflectivity embodiments of the optical measuring device seen in FIGS. 1 and 4.

As is known, $T = 1 - R$, where T equals the light transmitted through optically resonant structure 21, while R equals the reflectivity of optically resonant structure 21, as has been mentioned.

It then follows that the transmission curve for optically resonant structure 21 would be the same as its reflectivity curve, except it is 180° out of phase. That is, the transmission curve has a maxima where the reflectivity curve has a minima, and vice versa.

Shifting of the transmission curve right and/or left as a function of any of the optically sensitive physical characteristics of optically resonant structure 21 are again termed microshifts. In addition, all of the other definitions and explanations previously given regarding the reflectivity curve of optically resonant structure 21 and the reflectivity first and second embodiments of FIGS. 1 and 4 of the optical measuring device, such as regarding theory, operation, input measuring light, resonance cycle, and operating segment apply equally well to the transmission curve of optically resonant structure 21 and the transmission embodiments of FIGS. 13 and 14 of the optical measuring device, except for any differences apparent to those of ordinary skill in the art, such as that, regarding the transmission embodiment of FIG. 14, it is preferred that the length and the microshifting of the operating segment be centere around a minima on the transmission curve if it is desired to utilize the maximum length and the maximum microshifting possible without generating ambiguous spectrally modulated output light from spectral modulation sensor 22.

Turning now to the specific transmission embodiments of the spectral modulation sensor 22 seen in FIGS. 15-18a inclusive, they correspond, respectively, to the reflectivity embodiments of spectral modulation sensor 22 seen in FIGS. 8-8b and 10-12a, inclusive.

Figure 15:
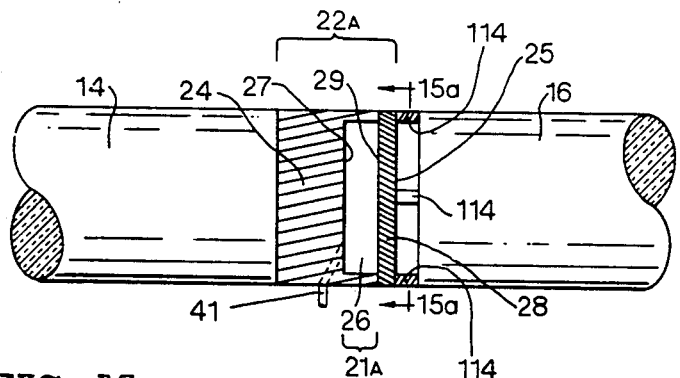
FIGS. 15, 15b, 16, 17 and 18 are schematic side elevation views of sensors 22A, 22Aa, 22B, 22C and 22D of FIGS. 8, 10, 11 and 12, respectively, being operated in a transmission mode, the views being partly in longitudinal cross sections taken along lines 15—15, 16—16, 17—17 and 18—18 of FIGS. 15a, 16a, 17a and 18a, respectively.
Figure 15C:
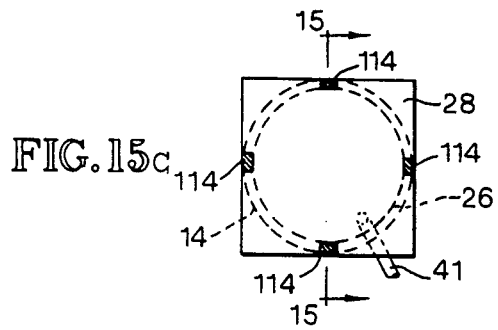
FIGS. 15a, 16a, 17a and 18a are cross sectional views taken along lines 15a—15a, 16a—16a, 17a—17a and 18a—18a of FIGS. 15, 16, 17 and 18 respectively.
Figure 15B:
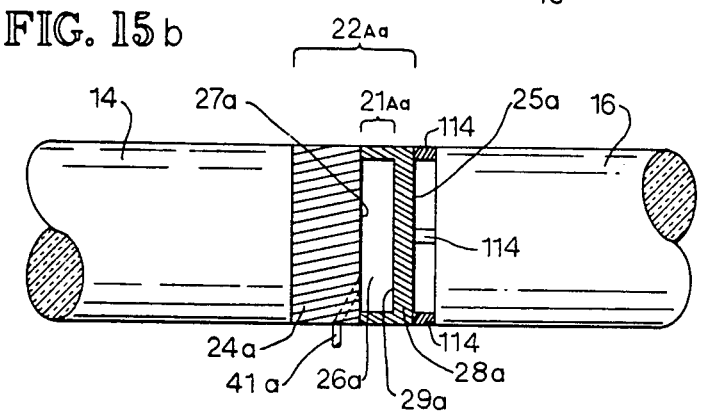
Figure 16:
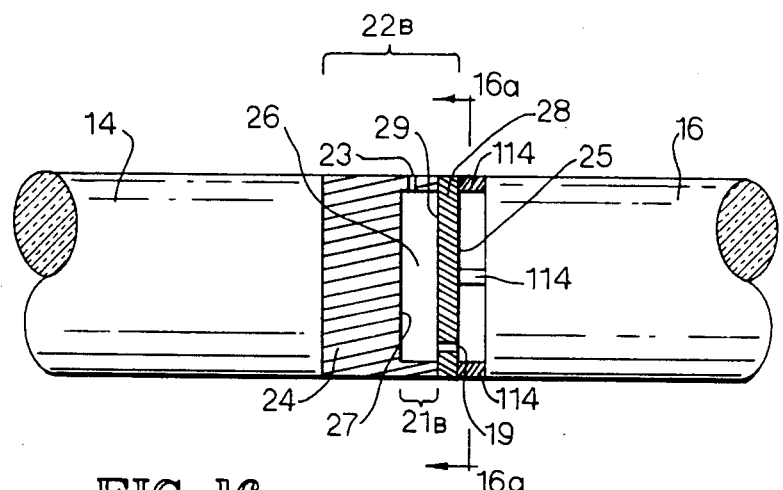
Figure 16A:
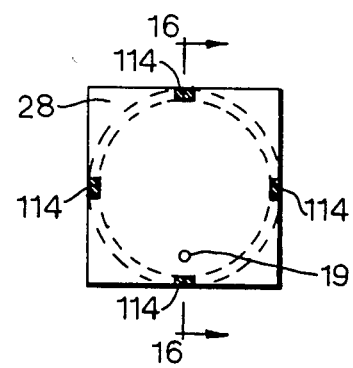

Regarding the transmission embodiments of spectral modulation sensor 22 seen in FIGS. 15-16a, inclusive, 18 and 18a, input optical fiber 14 is connected to one side of spectral modulation sensors 22A, 22Aa, 22B, and 22D as seen therein. As also seen therein, output optical fiber 16 is connected to and spaced away from the other side of spectral modulation sensors 22A, 22Aa, 22B, and 22D by one or more spacers 114. Spacers 114 also permit the environment access to the outer surface of covers 28, 108. Spacers 114 are by way of non-limiting example since any other form of connector/spacer which permitted optical and physical coupling of sensor 22 with output optical fiber 16, while allowing environmental access to the outer surface of covers 28, 108 would serve equally well.

Figure 17:
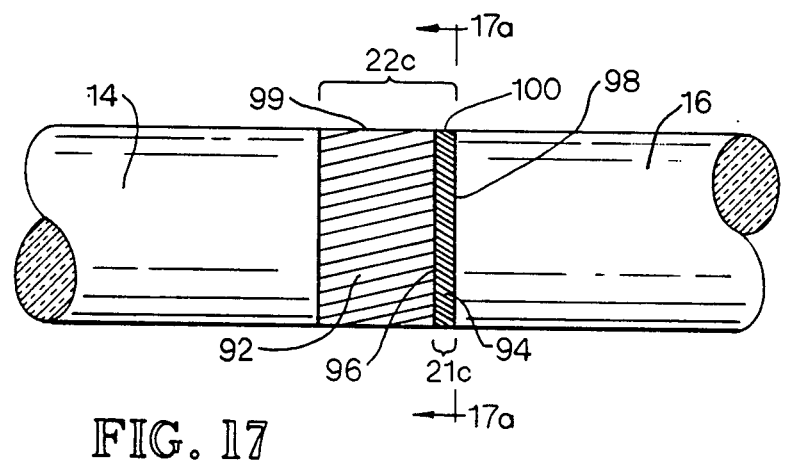
Figure 17A:
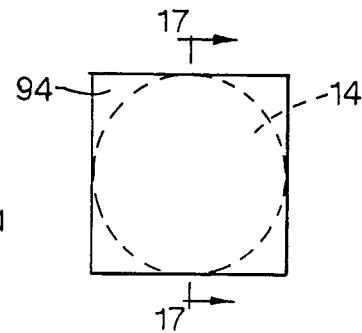
Figure 18:
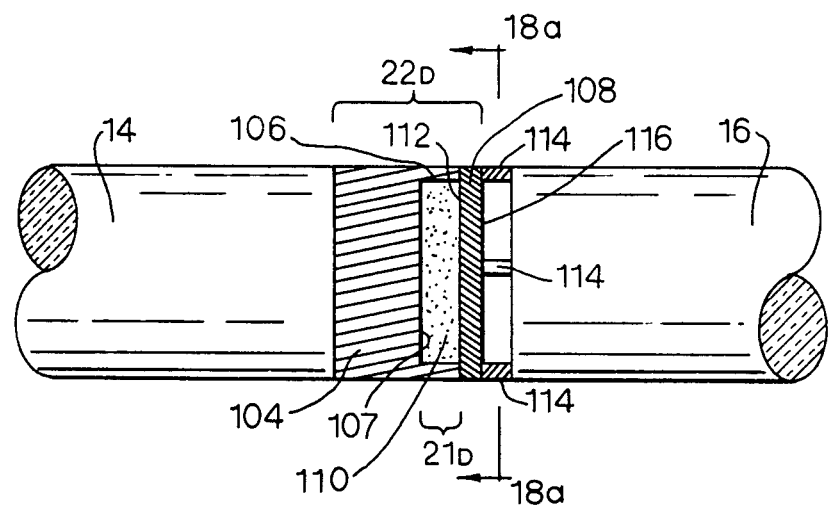
Figure 18A:
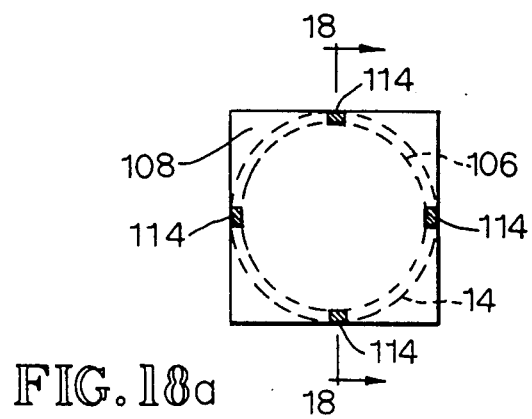

Regarding the transmission embodiment of the spectral modulation sensor 22C seen in FIGS. 17 and 17a, input and output optical fibers 14, 16, respectively, are connected to opposite sides of sensor 22C, as seen.

It is noted spectral modulation sensors 22A-22D seen in the transmission embodiments of FIGS. 15-18a are identical to spectral modulation sensors 22A-22D seen in the reflectivity embodiments of FIGS. 8-8b and 10-12a, respectively. The only difference between these transmission and reflectivity embodiments is the manner in which light is inputted to and outputted from them. Accordingly, everything said previously regarding sensors 22A-22D regarding the reflectivity embodiments of FIGS. 1-12a applies equally to the transmission embodiments of FIGS. 13-18a, except for any differences apparent to those of ordinary skill in the art, such as that outer surfaces 25, 25a, 98 and 116 of sensors 22A-22D would not have a light absorbing and/or excluding layer or cover applied to them regarding the transmission embodiments of FIGS. 13-18a, because to do so would prevent spectrally modulated output light from reaching output optical fiber 16.

Sixth Embodiment 22E of Spectral Modulation Sensor (Refractive Index/Chemical)

Reflection Form of Sixth Embodiment 22E

Turning now to FIGS. 19 and 20, a sixth embodiment 22E of spectral modulation sensor 22 is illustrated which is capable of sensing fluid refractive index with high resolution. This embodiment provides measurement capability of diverse parameters that can be correlated with fluid refractive index. By way of non-limiting examples, this can include fluid density, composition, mixture composition and solute concentration, and time dependent parameters such as dissolution and reaction rates. Refractive index sensor 22E uses the same operating principles as spectral modulation sensor 22 and spectral modulation pressure sensor 22A; and is the same in all respect in manufacture, assembly, construction, operation and use as sensors 22 and 22A, except for those express or implied differences which will be made apparent from the discussion below.

Sensor 22E comprises a substrate 120 having a microchannel 122, and a transverse cover 124. Optically resonant structure 21E comprises the portion of the at least partially reflective bottom 126 of channel 122 which is located beneath the at least partially reflective bottom 128 of cover 124; and also includes whatever is located therebetween in cavity 130 which is defined between the bottom 128 of cover 124 and the bottom 126 of microchannel 122. The portions of cavity 130 and reflective bottoms 126 and 128 of optically resonant structure 21E which are used to spectrally modulate the input measuring light are located, as seen, over optical fiber 14.

Substrate 120 is composed of a transparent material which is refractory and which is chemically resistant or inert with respect to the chemical(s) sensor 22E is designed to sense. Thus, by way of non-limiting example, substrate 120 may be composed of 7740 Pyrex glass. Microchannel 122 is preferably etched by a chemical wet etching process similar to that described above for etching cavity 26 in pressure sensor 22A. Applicants have discovered that such chemical wet etching process leaves the bottom 126 of microchannel 122 smooth and flat enough (to about 1/20th of the average wavelength of the input measuring light) to form an adequate reflective surface for optically resonant structure 21E.

The width of microchannel 122 is preferably equal to or greater than the diameter of optical fiber 14; while microchannel 122 has a depth (and reflective surfaces 126 and 128 of optically resonant structure 21E are separated by a distance) which must be less than the coherence length, as determined by the optical properties of either the light source(s) 48 or detectors 52, 62 and the refractive index range sensor 22E is designed to sense (see FIG. 4).

Coherence length = $(Lambda)^2$/(Source or detector bandwidth·average refractive index);

wherein "Lambda" is the average wavelength of the input measuring light being emitted by light source(s) 48 which is used for detection in sensor 22E, or is the average wavelength of the output measuring light from sensor 22E detected by detectors 54, 62; wherein "source bandwidth" is the bandwidth of the input measuring light from light sources(s) 48 used for detection in sensor 22E; wherein "detector bandwidth" is the bandwidth of the output measuring light being detected by detectors 54, 62; and wherein "average refractive index" is the average refractive index of the sensed chemical(s) located within cavity 130 of optically resonant structure 21E of sensor 22E.

By way of non-limiting example, the coherence length may typically be in the range of from ten to twenty times the average wavelength of the input measuring light.

Conventional vapor deposition techniques may be used to deposit on the bottom 126 of microchannel 122 an optional thin film of material that provides enhanced chemical resistance with respect to the chemical(s) sensor 22E is designed to sense, and to provide favorable optical qualities to bottom 126 of microchannel 122. Such favorable optical qualities would include, for example, the thin film having a high refractive index to help provide an at least partially reflective, mirror like quality to bottom 126 of microchannel 122, so bottom 126 becomes a good reflective surface for optically resonant structure 21E. By way of non-limiting example, such thin film may be about 200 Angstroms thick and be composed of titanium dioxide or silicon dioxide. Such thin film may have a thickness which is equal to several wavelengths of the average wavelength of the input measuring light, as long as the thin film is smooth and flat to about 1/20th of the average wavelength of the input measuring light, and the overall thickness of optically resonant structure 21E (the distance between its surfaces 126, 128) does not exceed the coherence length limitation discussed above.

Similarly, this kind of thin film may be deposited on the bottom 128 of cover 124 for similar reasons.

Cover 124 is composed of a material which is refractory and which is chemically resistant or inert with respect to the chemicals sensor 22E is adapted to sense. Thus, by way of non-limiting example, cover 124 may be composed of single crystal silicon. Cover 124 is bonded to substrate 126 by a method similar to that described earlier to bond cover 28 to substrate 24 of pressure sensor 22A. The width of cover 124 is preferably selected, as a minimum, to be about equal to the diameter of optical fiber 14. In general, as the width of cover 124 increases, the response time of sensor 22E decreases, and is not desireable unless a filtering function is a desired feature, as will be discussed below in due course.

Across for the sensed chemical to cavity 130 in optically resonant structure 21E is provided by the openings 123, 125 formed by microchannel 122 and cover 124 at the top and bottom edges of cover 124. With such a pair of openings 123, 125, when external means (not illustrated since they form no part of the present invention) are used to force the sensed chemical to flow into and out of cavity 130 in optically resonant structure 21E, one of the openings 123, 125 could form the inlet to cavity 130, while the other opening formed the outlet. As few as one, or more than two such openings 123, 125 to cavity 130 could be provided.

To provide a cover 124 having the desired width, normally cover 124 would initially have a width which was considerably wider than illustrated, for ease of manufacture. Then, after the initial, wider cover 124 is bonded to substrate 120, any excess of cover 124 is mechanically abraded away, as with a diamond wheel, to leave cover 124 with its desired width.

It should be noted that sensor 22E could be turned over so that its cover 124, instead of its substrate 120, was attached to optical fiber 14; and that microchannel 122 and cavity 130 could be formed entirely in cover 124, or partially in cover 124 and partially in substrate 120.

Turning now to FIGS. 21 and 22, a second embodiment 22E' of refractive index sensor 22E is seen which is the same, in all respects, as that shown in FIGS. 19 and 20, except for those differences, express or implied, made apparent by the discussion below. Accordingly, for clarity, the same reference numerals have been used for the features of sensor 22E' which are the same as those of sensor 22E, except that a prime has been appended thereto.

Sensor 22E' includes a pair of filter comb structures 132 located within michrochannel 126' and located on opposite sides of optical fiber 14. Each filter comb structure 132 comprises an array of filter elements 134, a total of 18 such filter elements 134 being illustrated, by way of non-limiting example.

Alternatively, a single filter comb structure 132 could be used, preferably on the inlet opening 123 or 125 side of optically resonant structure 21E'; or if optically resonant structure 21E' had but a single opening 123 or 125, filter comb structure 132 would then be located between its single opening 123 or 125 and optically resonant structure 21E'.

Filter elements 134 are preferably formed as an integral part of substrate 120' during the etching of microchannel 122' in substrate 120', by the use of the same photolithographic techniques used to mask off microchannel 126'. Preferably, the tops of filter elements 134 are coplanar with the top surface of the adjacent unetched portions of substrate 120', as seen, so that when cover 124' is bonded to substrate 120', cover 124' also bonds to the top of each filter element 134 to form a good seal therebetween. Cover 124' is made wide enough so that it will cover all of filter elements 134. By way of non-limiting example, the distance between adjacent filter elements 134 is preferably on the order of the depth of microchannel 122, or smaller, to prevent any objectionable particulate foreign matter in the sensed fluid from reaching the optically active central sensing portion of optically resonant structure 21E' which is located over input optical fiber 14.

Figure 23:
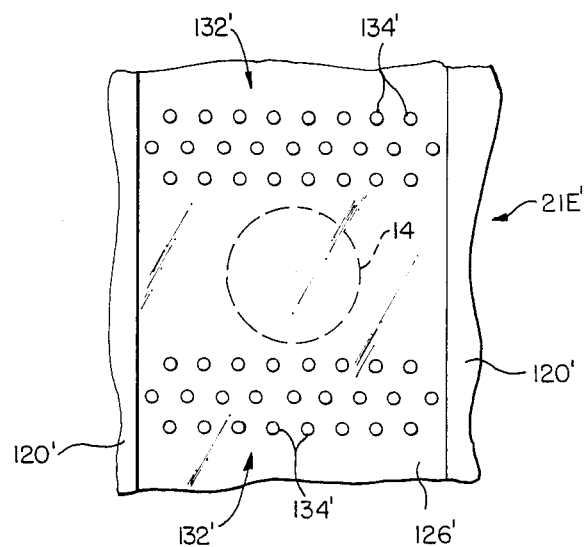
FIG. 23 is a view similar to that of FIG. 22 showing a modified embodiment 132' of filter comb structure 132.

An alternative form of filter comb structure 132 is shown as filter comb structure 132' in FIG. 23. Each filter comb structure 132' is composed of a close packed array of pin-like filter elements 134', a total of 46 such filter elements 134' being illustrated, by way of non-limiting example. Filter comb structure 132' may also be formed as a square array. The tops of filter elements 134' are preferably coplanar with the top of the unetched portions of substrate 120' for the same reasons expressed above regarding filter elements 134. The preferred spacing between adjacent filter elements 134' is as was discussed above regarding filter elements 134.

After fabrication, sensors 22E, 22E' are fused or adhesively mounted, by conventional techniques, to a probe structure containing optical fiber 14. Such probe structure is not illustrated since it forms no part of the present invention. Sensors 22E, 22E' are mounted so optical fiber 14 optically communicates with optically resonant structure 21E, 21E' via transparent substrate 120, 120'.

The operation of sensor 22E will now be addressed, it being understood that the operation of sensor 22E' would be the same.

In operation, the particular index of refraction of the particular sensed fluid within cavity 130 of optically resonant structure 21E produces a corresponding particular microshift in optically resonant structure 21E's reflectivity (or transmission) curve and operating segment(s) as a function of the refractive index of the sensed fluid. As a result, output light from optically resonant structure 21E is spectrally modulated by optically resonant structure 21E as a function of the refractive index of the sensed fluid, and thus carries accurate information regarding such refractive index which helps to identify the sensed fluid composition because the refractive indexes of many chemicals are different.

In use, when sensor 22E is inserted into the sensed fluid (which may be a liquid or a gas), microchannel 122 is primed with the fluid by surface tension if it is a liquid, or by any pressure difference which may be applied across microchannel 122 beneath cover 124. In general, when sensor 22E is exposed to a new fluid to be sensed, any fluid already present within cavity 130 in optically resonant structure 21E will equilibrate with the new fluid to be sensed by mass diffusion and/or forced flow. The extremely small size of the actively sensed volume of fluid within cavity 130 is highly desireable in this respect, since mass diffusion dominated equilibration is sensitive to the square of the diffusion length. That is, doubling the width of cover 124 undesireably increases the time to equilibrium by a factor of four.

Extremely high resolution (sensitivity) and a narrow range of refractive indexes to be sensed are generally desired for sensing composition in industrial chemical control applications. This is somewhat different than for pressure sensor 22A, where generally a moderate resolution (sensitivity) is desired over a wide range of pressure. In general, there is a trade off between resolution and range, with greater resolution resulting in less range, and vice versa.

Referring to FIG. 4, highest resolution is obtained when dual narrow bandwidth light sources 48 or dual monochromatic light sources 48 are used in conjunction with an extremely deep cavity 130 that has a depth less than the coherence length. For highest resolution, it is preferred that such dual input measuring light wavelength bands or wavelengths have a frequency separation which is broadly in the range of from less than about 0.1% to about 100% of the bandwidth of the resonance cycle of sensor 22E at the input measuring light wavelengths of interest, and which is, more narrowly, at multiples of about 50% (e.g. 50%, 100% 150%, etc.) of the bandwidth of the resonance cycle of sensor 22E at the input measuring light wavelengths of interest.

From a practical standpoint, however, operation with such very deep cavities 130 is not always desireable since thermal expansion effects of the materials comprising sensor 22E become increasingly difficult to control, particulate matter is more difficult to keep out of the optically active area of optically resonant structure 21E, and appropriate light sources 48 or narrowband detectors 52, 62 are difficult to implement.

A less difficult and reasonably sensitive ratiometric implementation is possible using a narrow band continuous light source 48 such as a light emitting diode (LED). To obtain the desired high resolution and narrow range desired for refractive index sensor 22E, sensor 22E is preferably supplied with input measuring light whose overall bandwidth is broadly in the range of about 1% to about 200% of the bandwidth of sensor 22E's resonance cycle at the input measuring light wavelengths of interest, and which is, more narrowly, in the range of about 10% to about 110% of sensor 22E's resonance cycle bandwidth at the input measuring light wavelengths of interest.

Figure 24:
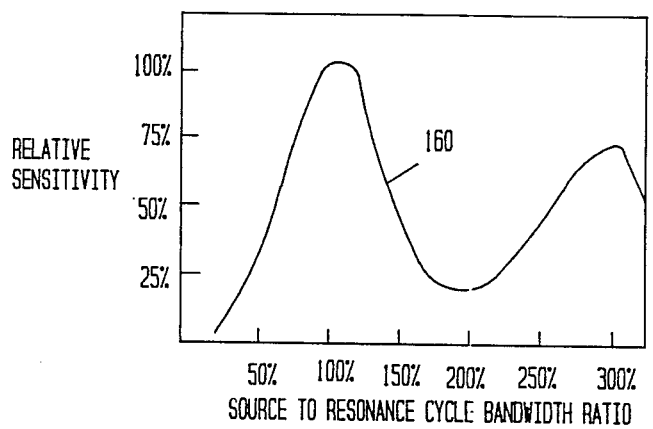
FIG. 24 illustrates graphically the relative sensitivity of sensors 22E, 22E' as their resonance cycle widths to light source bandwidth ratios change.

FIG. 24 shows in curve 160 the relative sensitivity (measured in arbitrary units) of refractive index sensor 22E as its resonance cycle bandwidth to input measuring light bandwidth ratio changes. As seen, there is clearly an optimum ratio from a sensitivity standpoint at a ratio of about 100%. Regarding FIG. 24, the average refractive index of the sensed fluid was 1.35, and the input measuring light bandwidth was 10% of the average input measuring light wavelength.

Figure 25:
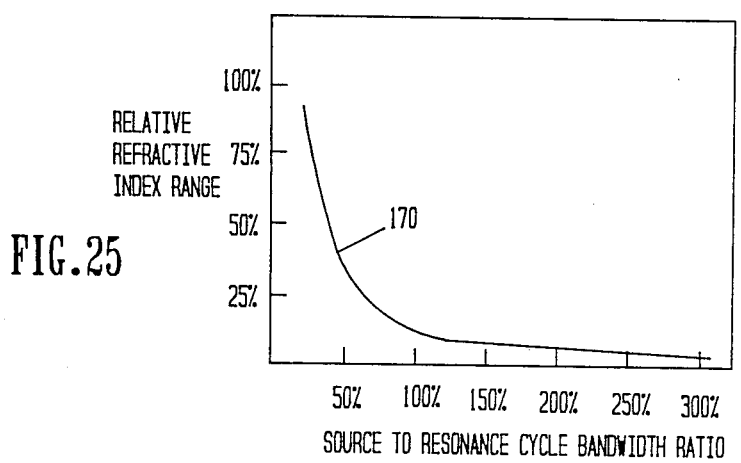
FIG. 25 illustrates graphically the effect on the refractive index working ranges of sensors 22E, 22E' of varying their resonance cycle widths to light source bandwidths ratios.

FIG. 25 shows in curve 170 the effect of varying sensor 22E's resonance cycle bandwidth to input measuring light bandwidth ratio on its relative refractive index working range (measured in arbitrary units). As seen, its working range is smaller as its sensitivity increases and its resonance cycle bandwidth to input measuring light bandwidth ratio approaches unit (100%). Regarding FIG. 25, the input measuring light bandwidth was 10% of the average input measuring light wavelength, and the average refractive index of the sensed fluid was 1.35.

In addition, when a single continuous light source 48 is used, such as an LED, the desired spectral separation of the output measuring light for ratiometric signal processing may be achieved through the use of filters 52, 60 on detectors 54, 62 (see FIG. 4) which separate the spectrally modulated output measuring light into two wavebands with an average spectral separation that is preferably in the range of about 1% to about 20% of the average input measuring light wavelength.

Figure 26:
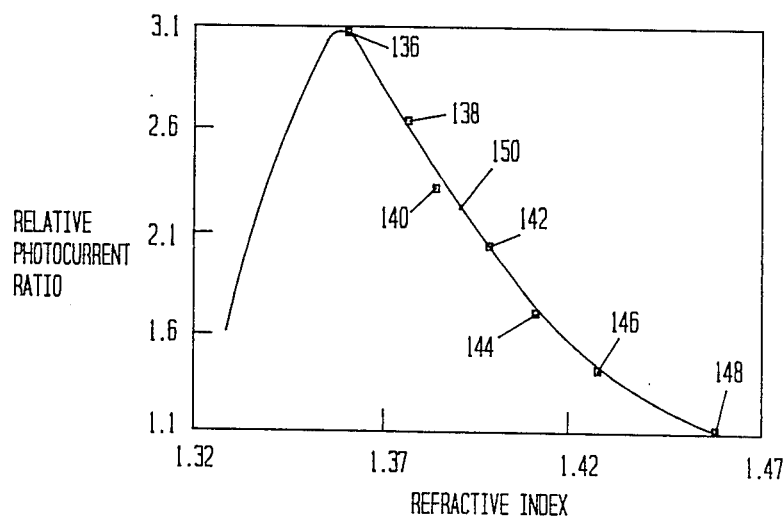
FIG. 26 illustrates graphically the relative output measuring photocurrent ratio of sensors 22E, 22E' as a function of the refractive indices of the sensed chemicals.

FIG. 26 shows actual data which was obtained when sensor 22E was substituted for sensor 22 in the ratiometric detection apparatus of FIG. 4. In FIG. 26, the relative output measuring photocurrent ratio from divider circuit 68 is plotted don the vertical axis while the refractive index of the sensed fluid is plotted on the horizontal axis to produce output curve 150. In the test, sensor 22E's optically resonant structure 21E had a cavity 130 which was 200 microns wide and 1.55 microns deep. There was a thin of titanium dioxide 200 Angstroms thick deposited on the bottom 126 of cavity 130, and a thin film of silicon dioxide 200 Angstroms thick on the bottom 128 of cover 124. Optical fiber 14 was 100 microns in diameter and cover 124 was 200 microns wide.

Light source 48 was an LED having a peak emission wavelength of 820 nm and a half-power bandwidth of 40 nm. Optical fiber 14 was quartz and had a diameter of 100 microns. Spectral separation of the spectrally modulated output measuring light from sensor 22 was achieved by selecting filters 52, 60 (see FIG. 4) that essentially split the spectrally modulated output measuring light into two side-by-side spectral components abutting at the 820 nm peak emission wavelength of LED light source 48. A unique one-to-one relationship obtained between sensor 22E's relative output measuring photocurrent ratio and refractive index is shown for the refractive index working ranges of from about 1.32 to about 1.36, and from about 1.36 to about 1.46. Sensor 22E, when used as seen in FIG. 4 with ratiometric signal processing, achieved a resolution of 1 part in 10,000 of refractive index over these working ranges using conventional photodetectors 54, 62 and state-of-the-art electronics for amplifiers 56, 66 and divider circuit 68.

In FIG. 26 data points 136-148 are for the sensed chemicals ethanol, 2-propanol, heptane, octane, decane, octanol, and cyclo-octaine, respectively.

Sensor 22E does not need to be coupled to light source 48 and dual detectors 54, 62 by optical fibers 12, 14, 16. Alternatively, there could be employed a conventional lens train system for focusing light from light source 48 onto sensor 22E's optically resonant structure 21E and a second conventional lens train system for delivering its spectrally modulated output light to beam splitter 50.

Sensor 22E or 22E' could also be used in lieu of sensor 22 in the non-ratiometric optical measuring device seen in FIG. 1. In such event all of the preceeding discussions relating in any way to the FIG. 1 embodiment apply equally well when sensor 22E or 22E' is used to replace sensor 22 therein.

Transmission Form of Sixth Embodiment 22E

Figure 27:
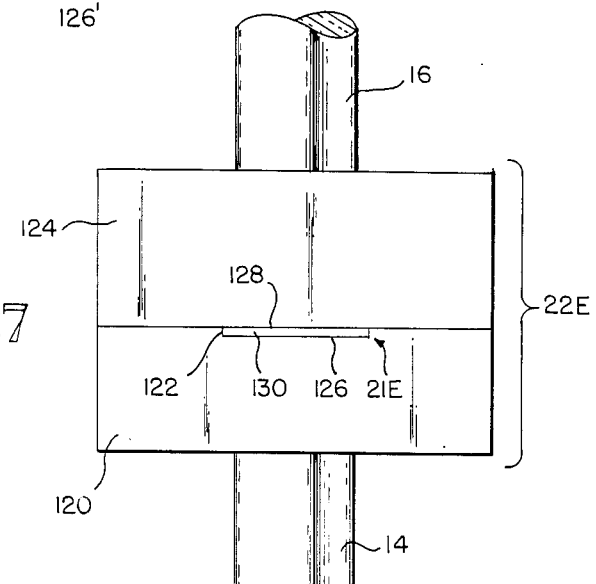
FIG. 27 is a side elevation view, taken along line 27—27 of FIG. 28, of a transmission form of spectral modulation sensor 22E.
Figure 28:
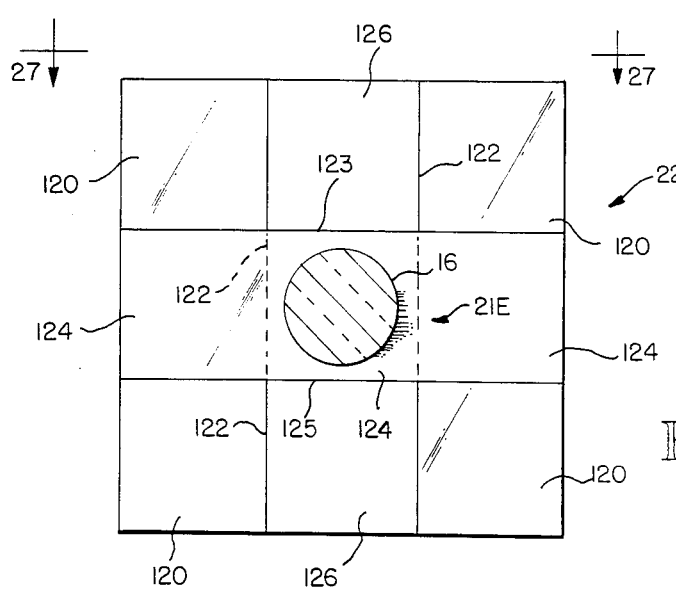
FIG. 28 is a top elevation view, partly in cross section, of sensor 22E seen in FIG. 27.

All of the remarks set forth earlier regarding the transmission embodiments of the optical measuring device and sensors 22A-22D (FIGS. 13-18a) apply equally well to the sixth embodiment of the spectral modulation sensor 22R, which is seen in a transmission embodiment in FIGS. 27 and 28. As seen, the transmission embodiment of sensor 22E of FIGS. 27 and 28 is identical to the reflection embodiment of sensor 22E seen in FIGS. 19 and 20, except for the added presence of output optical fiber 16 for conveying the spectrally modulated output light from sensor 22E to the detection means. Output optical fiber 16 is located directly opposite input optical fiber 14.

Similarly, the transmission form of sensor 22E' would also have its output optical fiber 16 secured to its cover 124' opposite its input optical fiber 14, and so is not illustrated, for clarity.

From the foregoing various further applications, modifications, and adaptations of the various apparatus and methods disclosed by the foregoing preferred embodiments of the present invention will be apparent to those skilled in the art to which it pertains, within the scope of the claims which are appended hereto. All embodiments, examples, alternatives and the like set forth herein are strictly by way of non-limiting example

What is claimed is:

1. An optical measuring device for measuring a range of values for a sensed physical parameter, wherein said optical measuring device comprises:
   light source means for emitting input measuring light of at least two wavelengths;
   optically resonant structure means;
   detection means; and
   light transmission means;
   wherein said optically resonant structure means has a reflectivity curve and a transmission curve, and has at least one operating segment on at least one of said reflectivity curve and said transmission curve;
   wherein said optically resonant structure means has an optically sensitive physical characteristic which changes as a function of said sensed physical parameter; wherein said changes of said optically sensitive physical characteristic microshift said at least one operating segment as a function of said sensed physical parameter;
   wherein said optically resonant structure means are for spectrally modulated said input measuring light as a function of said microshifts to produce spectrally modulated output light which is spectrally modulated as a function of said sensed physical parameter;
   wherein said at least one operating segment is selected to be less than about one resonance cycle in length for said range of values for said sensed physical parameter; wherein said at least one operating segment is microshifted less than about one resonance cycle over said range of values for said sensed physical parameter;
   wherein said wavelengths of said input measuring light are selected to fall at least substantially within said at least one operating segment over said range of values for said sensed physical parameter;
   wherein said at least one operating segment and said wavelengths of said input measuring light are selected such that over said range of values for said sensed physical parameter said spectrally modulated output light bears a unique one-to-one relationship to said sensed physical parameter;
   wherein said light transmission means are for conveying said input measuring light from said light source means to said optically resonant structure means and for conveying said spectrally modulated output light from said optically resonant structure means to said detection means;
   wherein said detection means are for deriving two electrical signals corresponding to any two different wavelength portions of said spectrally modulated output light; and are for taking the ratio of said two electrical signals to provide an output measuring electrical signal which is a function of said sensed physical parameter, to null errors in the measurement of the sensed physical parameter and to help to maximize both the useable length and the useable microshift of said at least one operating segment over said range of values for said sensed physical parameter;
   wherein said optically resonant structure means are for sensing the refractive index of a sensed fluid to measure and monitor at least one of said sensed fluid's density, composition, mixture composition and solute concentration;
   wherein said optically resonant structure means comprises a body defining a cavity having a pair of opposed reflective surfaces;
   wherein said body further defines opening means for permitting said sensed fluid to enter said cavity from outside of said optically resonant structure means; and
   wherein said optically sensitive physical characteristic is said index of refraction of said sensed fluid located within said cavity between said pair of opposed reflective surfaces.

2. An optical measuring device according to claim 1, wherein said body comprises a substrate and a cover at least one of which defines said cavity; wherein a first one of said pair of opposed reflective surfaces is a surface of said substrate facing said cover across said cavity; and wherein a second one of said opposed reflective surfaces is a surface of said cover facing said substrate across said cavity.

3. An optical measuring device according to claim 2, wherein a face of said substrate defines an elongated microchannel;
   wherein said cover overlies at least a portion of said microchannel;
   wherein said cavity is defined between said substrate and said cover, and comprises at least a portion of said microchannel;
   wherein one of said opposed reflective surfaces comprises a portion of a bottom of said microchannel; and
   wherein said microchannel extends outwardly from said cavity to at least a first edge of said cover to form said opening means for permitting said sensed fluid to enter said cavity from outside of said optically resonant structure means.

4. An optical measuring device according to claim 3, wherein said opening means are located adjacent said cavity to minimize the distance between said opening means and said cavity, to thereby minimize the amount of time it takes said sensed fluid to enter said cavity, to thereby minimize the response time of said optically resonant structure means to said sensed fluid.

5. An optical measuring device according to claim 3, wherein said microchannel in said substrate extends outwardly in at least two different directions from said cavity to said first edge of said cover and to a second edge of said cover, to form a first and a second said opening means to permit said sensed fluid to enter said cavity via said first opening means and to leave said cavity via said second opening means.

6. An optical measuring device according to claim 3, wherein said body further comprises at least one filter comb structure means, comprising a plurality of filter elements, for helping to prevent undesired foreign matter from entering said cavity along with said sensed fluid; and
   wherein said at least one filter comb structure means is located at least substantially in said microchannel between said opening means and said cavity, and wherein said filter comb structure means extends at least substantially between said bottom of said microchannel and said cover.

7. An optical measuring device according to claim 6, wherein said opening means are located adjacent said at least one filter comb structure means; and
   wherein said at least one filter comb structure means are, in turn, located adjacent said cavity, to minimize the distance between said opening means and said cavity, to thereby minimize the amount of time it takes said sensed fluid to enter said cavity, to thereby minimize the response time of said optically resonant structure means to said sensed fluid.

8. An optical measuring device according to claim 6, wherein at least some of said filter elements are integrally formed as part of at least one of said substrate and said cover.

9. An optical measuring device according to claim 1, wherein said input measuring light has a bandwidth in the range of from about 1% to about 200% of the bandwidth of a resonance cycle containing said at least one operating segment.

10. An optical measuring device according to claim 1, wherein said input measuring light has a bandwidth in the range of from about 10% to about 110% of the bandwidth of a resonance cycle containing said at least one operating segment.

11. An optical measuring device according to claim 1, wherein said at least two wavelengths of said input measuring light are selected such that a wavelength separation between said at least two wavelengths is in the range of from less than about 0.1% to about 100% of the bandwidth of a resonance cycle containing said at least one operating segment.

12. An optical measuring device according to claim 1, wherein said at least two wavelengths of said input measuring light are selected such that a wavelength separation between said at least two wavelengths is a multiple of about 50% of the bandwidth of a resonance cycle containing said at least one operating segment.

13. An optical measuring device according to claim 2, wherein said substrate and said light transmission means are at least substantially index matched.

14. An optical measuring device according to claim 13, wherein to help index match said substrate to said light transmission means, said substrate is selected to be made from borosilicate glass.

15. An optical measuring device according to claim 2, wherein said substrate has a thickness; and wherein to improve the sensitivity of said optically resonant structure, said thickness of said substrate is selected to be about equal to a diameter of said light transmission means.

16. An optical measuring device according to claim 2, wherein said body has an outer surface exposed to the environment; wherein to help prevent light transmitted through said optically resonant structure into said cover from reentering said optically resonant structure from said cover, and to help prevent external light from entering said optically resonant structure through said outer surface of said body, said outer surface of said body is at least substantially covered by a coating structure; wherein said coating structure is highly absorptive and non-reflective with respect to said wavelengths of said input measuring light; wherein said coating structure comprises at least two alternating layer; wherein each said layer comprises a different material; and wherein each said layer has a thickness which is substantially less than a shortest wavelength of said input measuring light.

17. An optical measuring device according to claim 16, wherein said at least two alternating layers comprise a layer of chrome about 25 Angstroms thick and a layer of silicon about 100 Angstroms thick.

18. A spectral modulation sensor for sensing a range of values for a sensed physical parameter; wherein said spectral modulation sensor comprises and optically resonant structure means; wherein said optically resonant structure means is adapted to receive input measuring light of at least one wave length from a light source means via a light transmission means;
   wherein said optically resonant structure means has a reflectively curve and a transmission curve, and has at least one operating segment on at least one of said reflectivity curve and said transmission curve;
   wherein said optically resonant structure has an optically sensitive physical characteristic which changes as a function of said sensed physical parameter; wherein said changes of said optically sensitive physical characteristic microshift said at least one operating segment as a function of said sensed physical parameter;
   wherein said optically resonant structure means are for spectrally modulating said input measuring light as a function of said microshifts to produce spectrally modulated output light which is spectrally modulated as a function of said sensed physical parameter;
   wherein said at least one operating segment is selected to be less than about one resonance cycle in length for said range of values for said sensed physical parameter; wherein said at least one operating segment is microshifted less than about one resonance cycle over said range of values for said sensed physical parameter;
   wherein said at least one wavelength of said input measuring light is selected to fall at least substantially within said at least one operating segment over said range of values for said sensed physical parameter;
   wherein said at least one operating segment and said at least one wavelength of said input measuring light are selected such that over said range of values for said sensed physical parameter said spectrally modulated output light bears a unique one-to-one relationship to said sensed physical parameter;
   wherein said optically resonant structure means are for sensing the refractive index of a sensed fluid to measure and monitor at least one of said sensed fluid's density, composition, mixture composition, and solute concentration;

wherein said optically resonant structure means comprises a body defining a cavity having a pair of opposed reflective surfaces;

wherein said body further defines opening means for permitting said sensed fluid to enter said cavity from outside of said optically resonant structure means; and wherein said optically sensitive physical characteristic is said index of refraction of said sensed fluid located within said cavity between said pair of opposed reflective surfaces.

19. A spectral modulation sensor according to claim 18, wherein said body comprises a substrate and a cover, at least one of which defines said cavity; wherein a first one of said pair of opposed reflective surfaces is a surface of said substrate facing said cover across said cavity; and wherein a second one of said opposed reflective surfaces is a surface of said cover facing said substrate across said cavity.

20. A spectral modulation sensor according to claim 19, wherein a face of said substrate defines an elongated microchannel;

wherein said cover overlies at least a portion of said microchannel;

wherein said cavity is defined between said substrate and said cover, and comprises at least a portion of said microchannel;

wherein one of said opposed reflective surfaces comprises a portion of a bottom of said microchannel; and wherein said microchannel extends outwardly from said cavity to at least a first edge of said cover to form said opening means for permitting said sensed fluid to enter said cavity from outside of said optically resonant structure means.

21. A spectral modulation sensor according to claim 20, wherein said opening means are located adjacent said cavity to minimize the distance between said opening means and said cavity, to thereby minimize the amount of time it takes said sensed fluid to enter said cavity, to thereby minimize the response time of said optically resonant structure means to said sensed fluid.

22. A spectral modulation sensor according to claim 20, wherein said microchannel in said substrate extends outwardly in at least two different directions from said cavity to said first edge of said cover and to a second edge of said cover, to form a first and a second said opening means to permit said sensed chemical to enter said cavity via said first opening means and to leave said cavity via said second opening means.

23. A spectral modulation sensor according to claim 20, wherein said body further comprises at least one filter comb structure means, comprising a plurality of filter elements, for helping to prevent undesired foreign matter from entering said cavity along with said sensed fluid; and wherein said at least one filter comb structure means is located at least substantially in said elongated microchannel between said opening means and said cavity, and wherein said filter comb structure means extends at least substantially between said bottom of said microchannel and said cover.

24. A spectral modulation sensor according to claim 23, wherein said opening means are located adjacent said at least one filter comb structure means; and wherein said at least one filter comb structure means are, in turn, located adjacent said cavity, to minimize the distance between said opening means and said cavity, to thereby minimize the amount of time it takes said sensed fluid to enter said cavity, to thereby minimize the response time of said optically resonant structure means to said sensed fluid.

25. A spectral modulation sensor according to claim 23, wherein at least some of said filter elements are integrally formed as part of at least one of said substrate and said cover.

26. A spectral modulation sensor according to claim 19, wherein said substrate and said light transmission means are at least substantially index matched.

27. A spectral modulation sensor according to claim 26, wherein to help index match said substrate to said light transmission means, said substrate is selected to be made from borosilicate glass.

28. A spectral modulation sensor according to claim 19, wherein said substrate has a thickness; and wherein to improve the sensitivity of said optically resonant structure, said thickness of said substrate is selected to be about equal to a diameter of said light transmission means.

29. A spectral modulation sensor according to claim 19, wherein said body has an outer surface exposed to the environment; wherein to help prevent light transmitted through said optically resonant structure into said cover from reentering said optically resonant structure from said cover, and to help prevent external light from entering said optically resonant structure through said outer surface of said body, said outer surface of said body is at least substantially covered by a coating structure; wherein said coating structure is highly absorptive and non-reflective with respect to said wavelengths of said input measuring light; wherein said coating structure comprises at least two alternating layers; wherein each said layer comprises a different material; and wherein each said layer has a thickness which is substantially less than a shortest wavelength of said input measuring light.

30. A spectral modulation sensor according to claim 29, wherein said at least two alternating layers comprise a layer of chrome about 25 Angstroms thick and a layer of silicon about 100 Angstroms thick.

* * * * *